US011732250B2

(12) United States Patent
Kline et al.

(10) Patent No.: US 11,732,250 B2
(45) Date of Patent: Aug. 22, 2023

(54) LIPASE ENZYMES

(71) Applicant: BASF SE, Ludwigshafen (DE)

(72) Inventors: Katie Kline, San Diego, CA (US); Adrienne Huston Davenport, San Diego, CA (US); Xuqiu Tan, San Diego, CA (US); Oliver Spangenberg, Ludwigshafen (DE); Claudia Esper, Ludwigshafen (DE); Amy Migliori, San Diego, CA (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 17/050,117

(22) PCT Filed: Apr. 24, 2019

(86) PCT No.: PCT/EP2019/060508
§ 371 (c)(1),
(2) Date: Oct. 23, 2020

(87) PCT Pub. No.: WO2019/206994
PCT Pub. Date: Oct. 31, 2019

(65) Prior Publication Data
US 2021/0095266 A1    Apr. 1, 2021

Related U.S. Application Data

(60) Provisional application No. 62/662,877, filed on Apr. 26, 2018.

(30) Foreign Application Priority Data

Sep. 14, 2018    (EP) ..................... 18194564

(51) Int. Cl.
  *C12N 9/20*    (2006.01)
  *C11D 3/386*   (2006.01)

(52) U.S. Cl.
  CPC ............ *C12N 9/20* (2013.01); *C11D 3/38627* (2013.01); *C11D 3/38663* (2013.01); *C12Y 301/01003* (2013.01)

(58) Field of Classification Search
None
See application file for complete search history.

(56) References Cited

U.S. PATENT DOCUMENTS 8,298,799 B2 * 10/2012 Bornscheuer ........... C12C 1/047
                                                    435/195

FOREIGN PATENT DOCUMENTS

WO    WO-2005/032496 A2    4/2005

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
International Application No. PCT/EP2019/060508, International Search Report and Written Opinion, dated Jun. 27, 2019.
"Environmental isolate hydrolase, SEQ ID No. 756", retrieved from EBI accession No. GSP:AEH47656, Database accession No. AEH47656 (Jul. 27, 2006).

* cited by examiner

*Primary Examiner* — Richard G Hutson
(74) *Attorney, Agent, or Firm* — Marshall, Gerstein & Borun LLP

(57) ABSTRACT

Engineered variant polypeptides having lipase enzyme activity, compositions comprising the enzymes, and methods of making and using the enzymes. The genetically engineered lipase enzymes are useful in many different applications such as laundry detergents, dish washing detergents, and cleaning products for homes, industry, vehicle care, baking, animal feed, pulp and paper processing, starch processing, biodiesel and ethanol production.

11 Claims, 2 Drawing Sheets
Specification includes a Sequence Listing.

```
                        SEQUENCE LISTING

<160> NUMBER OF SEQ ID NOS: 2

<210> SEQ ID NO 1
<211> LENGTH: 437
<212> TYPE: PRT
<213> ORGANISM: Unknown
<220> FEATURE:
<223> OTHER INFORMATION: Synthetically generated

<400> SEQUENCE: 1

Ala Thr Lys Ile Ser Asp Leu Gly Glu Val Tyr Thr Val Lys Thr Ala
1               5                   10                  15

Asp Gly Ile Thr Leu Lys Leu Leu Arg Tyr His Pro Pro Gly Gly Gln
            20                  25                  30

Pro Asn Ala Gly Ala Gln Pro Val Leu Leu Phe Ser Gly Leu Leu Cys
        35                  40                  45

Asn Met Asn Glu Phe Val Val Phe Thr Pro Asp Gly Leu Glu Ser Lys
    50                  55                  60

Tyr Lys Pro Tyr Tyr Pro Lys Glu Leu Ala Glu Trp Ala Lys Asp Asp
65                  70                  75                  80

Pro Tyr Ile Ala Lys Asp Pro Met Leu Tyr Tyr Ser Leu Ala His Tyr
                85                  90                  95

Leu Trp Lys Lys Gly Tyr Asp Val Trp Leu Leu Asn Tyr Arg Gly Thr
            100                 105                 110

Gly Val Gly Glu Met Lys Ser Gly Val Gly Asn Ala Arg Val Ser Leu
        115                 120                 125

Asp Val Trp Ala Leu Tyr Asp Val Pro Ala Ala Ile Asp Phe Val Asn
    130                 135                 140

Lys Lys Thr Gly Lys Ser Leu Ile Ile Gly His Ser Thr Gly Gly
145                 150                 155                 160

Leu Val Thr Tyr Val Tyr Leu Gln Gly Ala Lys Phe Val Lys Thr Pro
                165                 170                 175

Ser Cys Leu Ile Asn Leu Ala Trp Cys Glu Lys Val Ser Ala Ser Asp
            180                 185                 190

Ser Leu Ala Glu Glu Arg Asn Ser Lys Ile Val Gly Val Ile Ala Ile
        195                 200                 205

Asp Pro Ala Met Ile Pro Pro Leu Pro Lys Ile Leu Asp Thr Lys Ala
    210                 215                 220

Gly Trp Leu Leu Leu Asp Thr Pro Leu Tyr Ile Asp Leu Arg Asp Thr
225                 230                 235                 240

Ile Glu Thr Leu Ala Lys Lys Lys Gly Leu Trp Glu Ser Phe Leu Leu
                245                 250                 255
```

```
Thr Glu Lys Phe Leu Phe Glu Ala Ile Tyr Ser Leu Tyr Asn Arg Tyr
        260                 265                 270

Gly Glu Ile Ser Glu Ile Ile Lys Ala Leu Ala Phe Met Asn Pro Asn
        275                 280                 285

Asn Met Asn Pro Ala Leu Ser Asp Phe Met Thr Arg Tyr Val Ala Asp
290                 295                 300

Ser Leu Tyr Thr Pro Thr Leu Ala Gln Tyr Ala Asp Phe Gly Leu Arg
305                 310                 315                 320

Asn Thr Ala Arg Glu Tyr Phe Glu Asn Gly Lys Gly Tyr Leu Val
                325                 330                 335

Val Pro Pro Tyr Pro Arg Pro Gly Asp Gly Tyr Tyr Tyr Lys Gly
            340                 345                 350

Glu Asn Met Lys Lys Val Lys Val Pro Tyr Ile Thr Ile Leu Ser Glu
        355                 360                 365

Leu Pro Gly Leu Val Asp Ala Asn Gln Ile Ile Lys Asp Leu Met Gln
370                 375                 380

Ala Lys Thr Lys His Gln Leu Asp Arg Tyr Tyr Ile Ile Pro Gly Thr
385                 390                 395                 400

Gly His Leu Asp Val Ala Leu Gly Leu Asn Val Pro Thr Glu Val Phe
                405                 410                 415

Pro Lys Ile Gly Ala Trp Leu Asp Asp Leu Gln Glu Leu Ile Gly Tyr
            420                 425                 430

Pro Thr Thr Pro His
        435

<210> SEQ ID NO 2
<211> LENGTH: 1317
<212> TYPE: DNA
<213> ORGANISM: Unknown
<220> FEATURE:
<223> OTHER INFORMATION: Synthetically generated

<400> SEQUENCE: 2
gctactaaga tctccgatct gggtgaagtc tacaccgtca aaactgccga cggtatcacc      60
ctgaagttgt tgcgttacca cccaccaggt ggtcaaccta atgctggtgc tcagccagtc     120
ttgcttttct ccggtttgct gtgtaacatg aacgagttcg ttgttttcac cccagatgga     180
ttggaatcta agtacaagcc atattatcct aaggaattgg ccgagtgggc taaggacgac     240
ccttacatcg ctaaggaccc aatgttgtat tactcccttg ctcactactt gtggaagaag     300
ggttacgacg tttggcttct gaactaccgt ggtaccggtg tcgtgaaat gaagtccggt     360 gtcggtaacg ctagagtctc cttggacgtc tgggctttgt acgacgtccc agctgctatt     420
gactttgtta acaaaagac tggtaagtct tgattatcg gtggacattc taccggtgga     480
ttggttacct acgtttactt gcaaggtgct aagttcgtta agactccatc ctgtttgatt     540
aacctggcct ggtgtgaaaa agtctctgct tctgactcct ggccgaaga gagaaattct     600 aagatcgtcg gagtcattgc tattgatcct gctatgatcc ctccacttcc aaagattttg     660
gatactaagg ctggatggtt gttgttggac ccccttgt acattgacct tagagacacc     720
attgaaactt tggctaagaa gaagggtctg tgggagtctt ttctgcttac tgaaaagttt     780
ttgttcgagg ccatctactc tttgtacaac agatacggag aaatctctga gattatcaag     840
gctttggctt ttatgaaccc aaacaacatg aaccctgctc tgtccgattt catgactaga     900
tacgtcgccg actctttgta cactccaacc ttggcccaat acgccgactt cggtctgcgt     960
```

```
aatactgcca gagagtactt cgagaatggt ggtaaaggtt acttggtcgt cccaccatac    1020
ccaagaccag gagatggtta ttattactat aagggtgaga acatgaagaa ggtcaaggtc    1080
ccatacatta ccatcttgtc cgaactgcca ggtttggtcg acgctaacca aatcattaag    1140
gacttgatgc aagctaagac caagcaccaa ttggatagat attacatcat ccctggtacc    1200
ggtcacttgg atgttgcctt gggattgaac gtcccaactg aggttttccc aaagattggt    1260
gcttggttgg acgacctgca agaattgatc ggttatccta ctaccccaca ctgataa       1317
```

LIPASE ENZYMES

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "161154_Seqlisting.txt", which was created on Oct. 9, 2020 and is 5,943 bytes in size. The subject matter of the Sequence Listing is incorporated herein in its entirety by reference.

Genetically engineered lipase enzymes, compositions comprising the enzymes, and methods of using the enzymes or compositions comprising the enzymes. The genetically engineered lipase enzymes are useful in many different applications such as laundry detergents, dish washing detergents, and cleaning products for homes, industry, vehicle care, baking, animal feed, pulp and paper processing, starch processing, and ethanol production. Lipases have been employed in the removal of lipid stains and have been added to various compositions such as cleaning products. Current cleaning and/or fabric care compositions comprise formulations of many active ingredients that impact with the ability of lipases to remove lipid stains. Thus, the need exists for genetically engineered lipase enzymes that can function in the harsh environment of compositions used for cleaning.

DETAILED DESCRIPTION OF THE INVENTION

Figure 1:
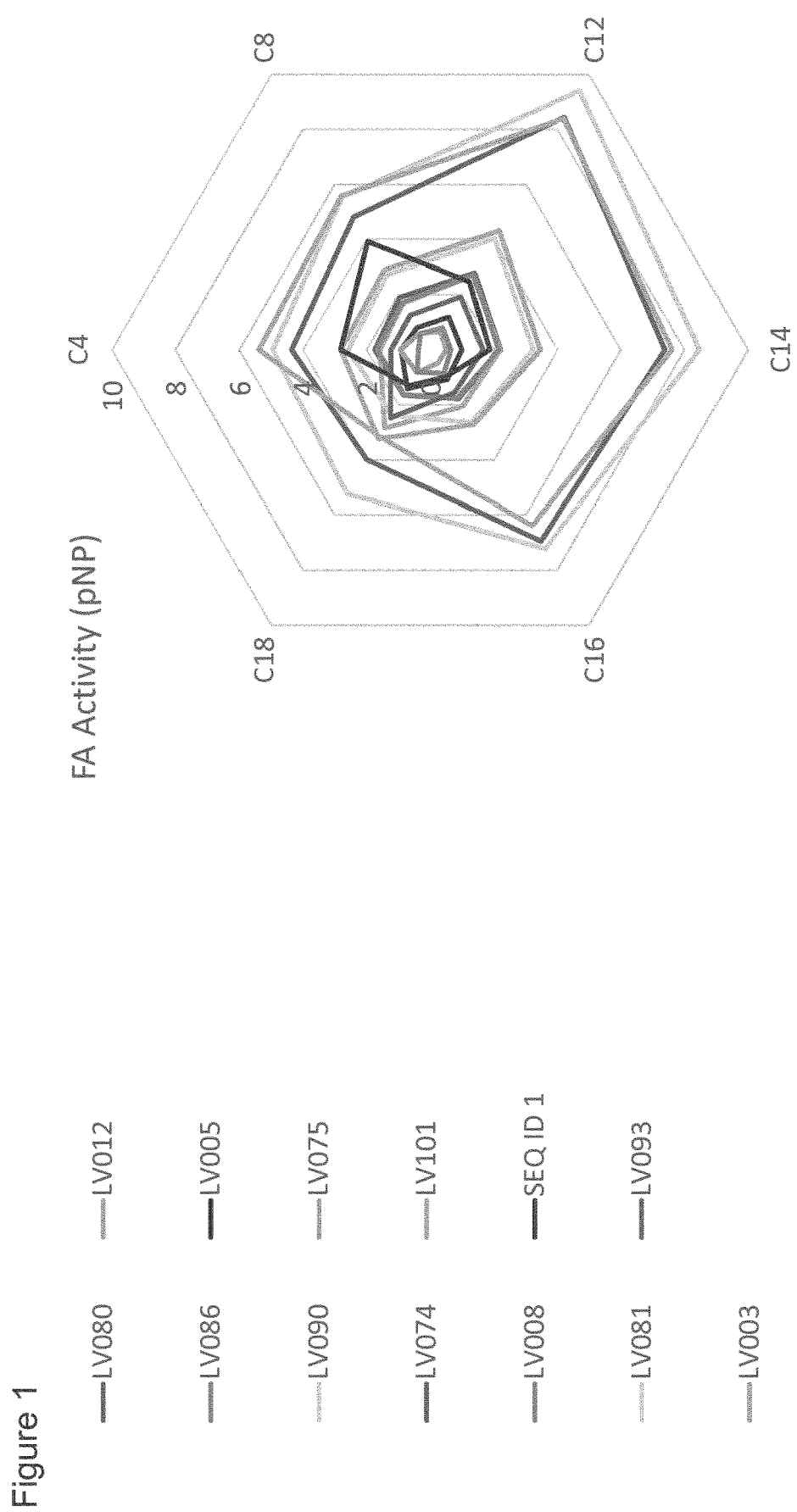
FIG. 1, shows the lipase enzymes fatty acid selectivity is across the different pNP substrates

An enzyme is a biological molecule (polypeptide) comprising a sequence of amino acid residues, wherein the enzyme can catalyze a reaction. Enzyme names are determined based on the recommendations of the Nomenclature Committee of the International Union of Biochemistry and Molecular Biology (IUBMB). Enzymes are defined by an EC (Enzyme Commission) number, recommended name, alternative names (if any), catalytic activity, and other factors. Enzymes are also known as a polypeptide, a protein, a peptide, or are described in patents and patent applications by a sequence identification number (SEQ ID NO.) Alternative names for enzyme can be used interchangeably.

Enzymes are obtained from or derived from many different sources including: plants; animals; bacteria, archaea, fungi, yeast, environmental samples containing DNA that encodes an enzyme, or enzymes can be synthetic generated in a laboratory. For example, bacterial sources of enzymes include enzymes derived from *Bacillus, Streptomyces, E. coli* and *Pseudomonas*, fungal sources of enzymes include enzymes derived from *Aspergillus, Fusarium, Thermomyces* and *Trichoderma*; yeast sources of enzymes include enzymes derived from *Pichia*, and *Saccharomyces*.

Different classes of enzymes are known to be useful in detergents and cleaning products including: lipase, amylase, protease, cellulase, mannanase, pectate lyase, and nuclease; however, there is a need in the industry to provide a lipase that has more activity, temperature profile, pH profile, has improved performance (stain removal), stability in presence of protease, reduces the amount of surfactant in a detergent formulation, no odor, or a combination thereof. The variant polypeptide lipase enzymes address these industrial needs.

The World Intellectual Property Office (WIPO) Standard ST.25 (1998) provides that the amino acid residues should be represented in the sequence listing using the following three-letter symbols with the first letter as a capital. The table below provides an overview of the amino acid identifiers as well as the corresponding DNA codons that encode the amino acid using the standard genetic standard. The DNA codons that encode amino acid residues can be different depending organism that is used and slightly different tables for translation of the genetic code may apply. A compilation of such non-standard code translation tables is maintained at the NCBI. For reference see e.g. https://www.ncbi.nlm.nih.gov/Taxonomy/Utils/wprintgc.cgi.

A "parent" polypeptide amino acid sequence is the starting sequence for introduction of mutations (e.g. by introducing one or more amino acid substitutions, insertions, deletions, or a combination thereof) to the sequence, resulting in "variants" of the parent polypeptide amino acid sequences. A parent includes: A wild-type polypeptide amino acid sequence or synthetically generated polypeptide amino acid sequence that is used as starting sequence for introduction of (further) changes. The parent polypeptide herein is a polypeptide having an amino acid sequence according to SEQ ID NO: 1.

A "variant polypeptide" refers to an enzyme that differs from its parent in its amino acid sequence. While the definition below describes variants in the context of amino acid changes, nucleic acids may be similarly modified, e.g. by substitutions.

The invention relates to a variant polypeptide having lipase activity comprising an amino acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence of SEQ ID NO:1. In one embodiment, said variant polypeptide has an increase in at least one characteristic selected from enzyme activity, pH-stability, stability against proteolytic degradation and stability in detergent formulation, or any combination thereof when compared to a *Thermomyces lanuginosa* lipase according to amino acids 1-269 of SEQ ID NO: 2 of U.S. Pat. No. 5,869,438 and/or when compared to a *Thermomyces lanuginosa* lipase according to amino acids 1-269 of SEQ ID NO: 2 of U.S. Pat. No. 5,869,438 with amino acid substitutions T231R and N233R.

In one embodiment, the variant polypeptide having lipase activity comprising an amino acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence of SEQ ID NO:1 has an increase in at least one characteristic selected from enzyme activity, pH-stability, stability against proteolytic degradation and stability in detergent formulation, or any combination thereof when compared to a lipase according to SEQ ID NO: 1.

The variant polypeptide of the invention may comprise changes selected from amino acid residue insertion, deletion, or substitution. Said variant polypeptide may comprise at least one substitution at least one of the following amino acid residue positions: 14, 64, 67, 79, 145, 263, 265, 266, 272, 275, 291, 293, 297, 298, 303, 307, 308, 310, 340, 347, 375, 377, 405, 407, or any combination thereof to the amino acid sequence of SEQ ID NO:1. The number of positions is based on the amino acid sequence provided as SEQ ID NO:1.

Specifically, the variant polypeptide of the invention may comprise at least one amino acid substitution selected from K14E, F56C, K64V, K64T, K64E, P67L, W79F, W79I, K145W, K145E, E263L, I265T, I265L, Y266L, Y266V, N272P, R273Q, Y275F, N291A, N291L, N291F, A293V, F297L, M298F, A303Q, S307L, L308S, L308N, T310Q, Y340F, Y347K, V375G, Q377K, L407A, and L407G. In one embodiment, the variant polypeptide comprises more than one of said substitutions.

The invention relates to a variant polypeptide having lipase activity, wherein the variant polypeptide is an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence as set forth in SEQ ID NO:1, wherein the variant polypeptide has a combination of amino acid modifications to the amino acid sequence of SEQ ID NO:1 selected from the group consisting of: (a1) N291A, 405L; (b1) W79F, I265L, N291L; (c1) E263L, T310Q; (d1) T310Q, L407A; (e1) K145E, L407A; (f1) K64V, L407A; (g1) M298F, L407A; (h1) K145E, Y340F; (i1) T310Q, L407A; (j1) T310Q, L407A; (k1) K14E, K64V, K145E, T310Q, L407A; (l1) K64V, K145E, M298F, T310Q, L407A; (m1) E263L, F297L, T310Q, L407A; (n1) E263L, F297L, T310Q, L407G; (o1) P67L, E263L, F297L, T310Q; (p1) F297L, T310Q; (q1) E263L, F297L; (r1) E263L, Q377K, T310Q, L407A; (s1) E263L, Q377K, T310Q, L407G; (t1) K14E, E2363L, I265T, A303Q, T310Q; (u1) E263L, T310Q, L407A; (v1) E263L, T310Q, L407G; (w1) E263L, M298F, T310Q; (x1) K145E, E263L, A303Q, T310Q, L407A; (y1) K145E, E263L, A303Q, T310Q, L407G; (z1) K64V, K145E, E263L, A303Q, T310Q; (a2) K145E, E263L, A303Q; (b2) K145E, A303Q; (c2) K145E, Y340F, Y347K, L407A; (d2) K145E, T310Q; (e2) K145E, E263L; (f2) K145E, Y347K; (g2) K145E, K64V; (h2) K145E, Y266L, A303Q; (i2) K145E, E263L, M298F, T310Q, L407A; (j2) K145E, E263L, M298F, T310Q, L407G; (k2) K145E, E263L, T310Q, L407A; (l2) K145E, E263L, T310Q, L407G; (m2) K14E, A303Q, L407A; (n2) K14E, E263L, A303Q, T310Q, L407A; (o2) K145W, E263L, I265T, A303Q, T310Q, L407A; (p2) K145W, I265T, A303Q, L407A; (q2) K64V, K145W, E263L, T310Q, L407A; (r2) K64V, K145W, E263L, M298F, T310Q; (s2) K64V, K145W, E263L, Y266L, T310Q; (t2) A303Q, L407A; (u2) M298F, L407G; (v2) I265T, M298F, L407A; (w2) I265T, M298F, L407G; (x2) Y266L, M298F, L407A; (y2) Y266L, M298F, L407G; (z2) P67L, F297L, L407A; (a3) P67L, F297L, L407G; (b3) I265T, L407A; (c3) Y266L, L407G; (d3) E263L, L407A; (e3) K145E, Y340F; (f3) K145E, Y340F; (g3) K145E, Y340F; (h3) K14E, A303Q, L407A; (i3) K14E, A303Q, L407A; (j3) K14E, A303Q, L407A; and (k3) K14E, K64V, K145E, M298F, T310Q, L407A.

The invention relates to a variant polypeptide having lipase activity, wherein the variant polypeptide is an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence as set forth in SEQ ID NO:1, and the variant polypeptide has an increase in enzyme activity, pH-stability, stability against proteolytic degradation and stability in detergent formulation, or any combination thereof when compared to the lipase of SEQ ID NO:1.

"Substitutions" are described by providing the original amino acid followed by the number of the position within the amino acid sequence, followed by the substituted amino acid. A specific amino acid residue may be substituted with any of the 19 amino acid residues different from the original one. For example, the substitution of histidine at position 120 with alanine is designated as "His120Ala" or "H120A".

Amino acid deletions are described by providing the original amino acid of the parent enzyme followed by the number of the position within the amino acid sequence, followed by*.

Amino acid insertions are described by providing the original amino acid of the parent enzyme followed by the number of the position within the amino acid sequence, followed by the original amino acid and the additional amino acid. For example, an insertion at position 180 of lysine next to glycine is designated as "Gly180GlyLys" or "G180GK".

The invention relates to fragments of the variant polypeptides, wherein said polypeptide fragments have lipase activity.

A "fragment", or "subsequence" as used herein are a portion of an amino acid sequence, wherein the fragments or subsequences retain at least one functional activity of the sequence to which it is related.

In one embodiment, the term "functional fragment" refers to any amino acid sequence which comprises merely a part of the full length amino acid sequence of the variant polypeptide of the invention, but still has the same or similar activity and/or function. The fragment comprises at least 70%, at least 80%, at least 85%, at least 90%, at least 95%, at least 96%, at least 97%, at least 98%, at least 99% of the original sequence. The functional fragment comprises contiguous amino acids compared to the original amino acid sequence.

The invention relates to a variant polypeptide having lipase activity, wherein the variant comprises a hybrid of at least one variant polypeptide of the invention, and a second polypeptide having lipase activity, wherein the hybrid has lipase activity. A "hybrid" or "chimeric" or "fusion protein" means that a fragment of the amino acid sequence of a first enzyme is combined with a fragment of the amino acid sequence of a second enzyme to form a hybrid enzyme wherein the hybrid has an enzyme activity.

The hybrid enzymes can be engineered with functional fragments from amino acid sequences of more than two enzymes. The hybrid may comprise a catalytic domain of a lipase of this invention and one or more catalytic domains of lipases commercially available such as: Lipolase™, Lipex™, Lipolex™ and Lipoclean™ (Novozymes NS), Lumafast (originally from Genencor) and Lipomax (Gist-Brocades/now DSM), wherein the hybrid has lipase activity.

In one embodiment, at least one functional fragment of an inventive lipase is combined with at least one functional fragment of a lipase selected from fungal triacylglycerol lipase (EC class 3.1.1.3). Fungal triacylglycerol lipase may be selected from a lipase of *Thermomyces lanuginosa*. In one embodiment, *Thermomyces lanuginosa* lipase is selected from triacylglycerol lipase according to amino acids 1-269 of SEQ ID NO: 2 of U.S. Pat. No. 5,869,438 or a variant thereof.

*Thermomyces lanuginosa* lipase may be selected from variants comprising at least the following amino acid substitutions when compared to amino acids 1-269 of SEQ ID NO: 2 of U.S. Pat. No. 5,869,438: T231R and N233R. Said *Thermomyces lanuginosa* lipase variants may further comprise one or more of the following amino acid exchanges when compared to amino acids 1-269 of SEQ ID NO: 2 of U.S. Pat. No. 5,869,438: Q4V, V60S, A150G, L227G, P256K.

*Thermomyces lanuginosa* lipase may be selected from variants comprising at least the amino acid substitutions T231R, N233R, Q4V, V60S, A150G, L227G, P256K within the polypeptide sequence of amino acids 1-269 of SEQ ID NO: 2 of U.S. Pat. No. 5,869,438.

*Thermomyces lanuginosa* lipase may be selected from variants comprising the amino acid substitutions T231R and N233R within amino acids 1-269 of SEQ ID NO: 2 of U.S. Pat. No. 5,869,438 and are at least 95%, at least 96%, at least 97%, at least 98%, or at least 99% similar when compared to the full-length polypeptide sequence of amino acids 1-269 of SEQ ID NO: 2 of U.S. Pat. No. 5,869,438. *Thermomyces lanuginosa* lipase may be a lipase according to amino acids 1-269 of SEQ ID NO: 2 of U.S. Pat. No. 5,869,438 with amino acid substitutions T231R and N233R.

The variant polypeptide of the invention is a "mature polypeptide" meaning an enzyme in its final form including any post-translational modifications, glycosylation, phosphorylation, truncation, N-terminal modifications, C-terminal modifications, signal sequence deletion. A mature polypeptide can vary depending upon the expression system, vector, promoter, and/or production process.

"Enzymatic activity" means at least one catalytic effect exerted by an enzyme. Enzymatic activity is expressed as units per milligram of enzyme (specific activity) or molecules of substrate transformed per minute per molecule of enzyme (molecular activity). Enzymatic activity can be specified by the enzymes actual function, e.g. proteases exerting proteolytic activity by catalyzing hydrolytic cleavage of peptide bonds, lipases exerting lipolytic activity by hydrolytic cleavage of ester bonds, etc.

The variant polypeptide of the invention exerts lipolytic activity or lipase activity, which may be provided in lipolytic units (LU). For example, 1 LU may correspond to the amount of lipase which produces 1 μmol of titratable fatty acid per minute in a pH stat. under the following conditions: temperature 30° C.; pH=9.0; substrate may be an emulsion of 3.3 wt. % of olive oil and 3.3% gum arabic, in the presence of 13 mmol/l $Ca^{2+}$ and 20 mmol/l NaCl in 5 mmol/l Tris-buffer.

The methods for determining lipolytic activity are well-known in the literature (see e.g. Gupta et al. (2003), Biotechnol. Appl. Biochem. 37, p. 63-71). E.g. the lipase activity may be measured by ester bond hydrolysis in the substrate para-nitrophenyl palmitate (pNP-Palmitate, C:16) and releases pNP which is yellow and can be detected at 405 nm.

Enzymatic activity may change during storage or operational use of the enzyme. The term "enzyme stability" relates to the retention of enzymatic activity as a function of time during storage or operation. The term "storage" herein means to indicate the fact of products or compositions or formulations being stored from the time of being manufactured to the point in time of being used in final application. Retention of enzymatic activity as a function of time during storage in detergent may be called "storage stability" herein. Storage may mean storage for at least two, at least 7, at least 14, at least 21, or at least 28 days at a storage temperature of 37° C. In one embodiment, storage means storage of a detergent formulation comprising at least one enzyme selected from the polypeptide of the invention.

In an aspect of the invention, storage means storage of a detergent formulation comprising at least two enzymes, wherein one enzyme is selected from the polypeptide of the invention and the second enzyme is selected from at least one protease. In one embodiment at least one protease is a subtilisin which is selected from SEQ ID NO: 22 as described in EP1921147 and variants thereof having proteolytic activity. The variant of SEQ ID NO: 22 as described in EP1921147 may be a polypeptide sequence which is at least 80% identical or similar to SEQ ID NO:22 as described in EP 1921147 and has proteolytic activity. In one embodiment, a subtilisin is at least 80% identical or similar to SEQ ID NO:22 as described in EP 1921147 and is characterized by having amino acid glutamic acid (E), or aspartic acid (D), or asparagine (N), or glutamine (Q), or alanine (A), or glycine (G), or serine (S) at position 101 (according to BPN' numbering) and has proteolytic activity. In one embodiment, subtilisin is at least 80%, at least 85%, at least 90%, at least 91%, at least 92%, at least 93%, at least 94%, at least 95%, at least 96%, at least 97%, at least 98% or at least 99% identical or similar to SEQ ID NO:22 as described in EP 1921147 and is characterized by having amino acid glutamic acid (E), or aspartic acid (D), at position 101 (according to BPN' numbering) and has proteolytic activity. In one embodiment, the subtilisin is SEQ ID NO:22 as described in EP 1921147 characterized by an amino acid substitution at position 101, such as R101E or R101D, alone or in combination with one or more substitutions at positions 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and/or 274 (according to BPN' numbering) and has proteolytic activity. In one embodiment, the subtilisin variant comprises an amino acid substitution at position 101, such as R101E or R101D and one or more further substitutions: (a) threonine at position 3 (3T), (b) isoleucine at position 4 (4I), (c) alanine, threonine or arginine at position 63 (63A, 63T, or 63R), (d) aspartic acid or glutamic acid at position 156 (156D or 156E), (e) proline at position 194 (194P), (f) methionine at position 199 (199M), (g) isoleucine at position 205 (205I), (h) aspartic acid, glutamic acid or glycine at position 217 (217D, 217E or 217G), (i) combinations of two or more amino acids according to (a) to (h).

To determine and quantify changes in catalytic activity of enzymes stored or used under certain conditions over time, the "initial enzymatic activity" is measured under defined conditions at time cero (100%) and at a certain point in time later (x %). By comparison of the values measured, a potential loss of enzymatic activity can be determined in its extent. The extent of enzymatic activity loss determines an enzymes stability or non-stability.

Parameters influencing the enzymatic activity of an enzyme and/or storage stability and/or operational stability are for example pH, temperature, and presence of oxidative substances:

A variant polypeptide is active over a broad pH at any single point within the range from about pH 4.0 to about pH 12.0. The variant polypeptides enzyme may be active over a range of pH 4.0 to pH 11.0, pH 4.0 to pH 10.0, pH 4.0 to pH 9.0, pH 4.0 to pH 8.0, pH 4.0 to pH 7.0, pH 4.0 to pH 6.0, or pH 4.0 to pH 5.0. The variant polypeptides may be active at pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6 pH 8.7, pH 8.8 pH 8.9, pH 9.0, pH 9.1, pH 9.2, pH 9.3, pH 9.4, pH 9.5, pH 9.6, pH 9.7, pH 9.8, pH 9.9, pH 10.0, pH 10.1, pH 10.2, pH 10.3, pH 10.4, pH 10.5, pH 10.6, pH 10.7, pH 10.8, pH 10.9, pH 11.0, pH 11.1, pH 11.2, pH 11.3, pH 11.4, pH 11.5, pH 11.6, pH 11.7, pH 11.8, pH 11.9, pH 12.0, pH 12.1, pH 12.2, pH 12.3, pH 12.4, and pH 12.5, pH 12.6, pH 12.7, pH 12.8, pH 12.9, and higher.

A "pH stability", refers to the ability of an enzyme to exert enzymatic activity at a specific pH range.

The variant polypeptides are active over a broad temperature, wherein the temperature is any point in the range from about 10° C. to about 60° C. The variant polypeptides may be active at a temperature range from 10° C. to 55° C., 10° C. to 50° C., 10° C. to 45° C., 10° C. to 40° C., 10° C. to 35° C., 10° C. to 30° C., or 10° C. to 25° C. The variant polypeptides may be active at a temperature range from 20° C. to 55° C., 20° C. to 50° C., 20° C. to 45° C., 20° C. to 40° C., 20° C. to 35° C., 20° C. to 30° C., or 20° C. to 25° C. The variant polypeptides may be active at a temperature of at least 10° C., 11° C. 12° C., 13° C., 14° C., 15° C., 16° C., 17° C., 18° C., 19° C., 20° C., 21° C. 22° C., 23° C., 24° C., 25° C., 26° C., 27° C., 28° C., 29° C., 30° C., 31° C. 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., or higher temperatures.

The terms "thermal stability" and "thermostability" refer to the ability of a protein to exert catalytic activity at a specific temperature, or within a temperature range. Enzymes generally have a finite range of temperatures at which they exert catalytic activity. In addition to enzymes that exert catalytic activity in mid-range temperatures (e.g., room temperature), there are enzymes that are capable of exerting catalytic activity in very high or very low temperatures. Thermostability may be characterized by what is known as the T50 value (a/so called half-life, see above). The T50 indicates the temperature at which 50% residual enzymatic activity is still present after thermal inactivation for a certain time when compared with a reference sample which has not undergone thermal treatment.

The terms "thermal tolerance" and "thermotolerance" refer to the ability of a protein to exert catalytic activity after exposure to a particular temperature, such as a very high or very low temperature. A thermotolerant protein may not exert catalytic activity at the exposure temperature, but exerts catalytic activity once returned to a favorable temperature.

The invention further relates to a polynucleotide encoding the variant polypeptides of the invention. The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length. A "gene" is a DNA segment carrying a certain genetic information.

A "parent" polynucleotide sequence is the starting sequence for introduction of mutations to the sequence, resulting in "variants" of said parent polynucleotide sequence. The parent polynucleotide sequence is a polynucleotide sequence according to SEQ ID NO: 2. A "variant polynucleotide" refers to a polynucleotide that encodes the same enzyme as the parent polynucleotide does. The variant polynucleotide in this case differs from its parent polynucleotide in its nucleic acid sequence, however the polypeptide encoded remains unchanged.

The variant polynucleotide of the invention in one aspect has a nucleic acid sequence which is at least 80% identical or similar when compared to the full length polynucleotide sequence of SEQ ID NO:2. The variant polynucleotide of the invention may have a nucleic acid sequence which is at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar when compared to the full length polynucleotide sequence of SEQ ID NO:2.

In one embodiment, the variant polynucleotide which is at least 80% identical or similar when compared to the full-length polynucleotide sequence of SEQ ID NO:2, encodes a polypeptide sequence having lipase activity comprising an amino acid sequence that is at least at least 80% identical or similar to the full length amino acid sequence of SEQ ID NO:1.

A variant polynucleotide according to the invention encodes a polypeptide having lipase activity comprising an amino acid sequence that is at least at least 80% identical or similar to the full length amino acid sequence of SEQ ID NO:1. The polynucleotide of the invention may encode a polypeptide having lipase activity comprising an amino acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence of SEQ ID NO:1.

In one embodiment, the variant polynucleotide of the invention encodes a polypeptide having lipase activity comprising an amino acid sequence that is at least at least 80% identical or similar to the full length amino acid sequence of SEQ ID NO:1 which comprises an amino acid residue insertion, deletion, or substitution to the amino acid sequence of SEQ ID NO:1. The amino acid residue insertion, deletion, or substitution may be at the amino acid residue position number 14, 64, 67, 79, 145, 263, 265, 266, 272, 275, 291, 293, 297, 298, 303, 307, 308, 310, 340, 347, 375, 377, 405, 407, or any combination thereof. An amino acid substitution may be selected from K14E, F56C, K64V, K64T, K64E, P67L, W79F, W79I, K145W, K145E, E263L, I265T, I265L, Y266L, Y266V, N272P, R273Q, Y275F, N291A, N291L, N291F, A293V, F297L, M298F, A303Q, S307L, L308S, L308N, T310Q, Y340F, Y347K, V375G, Q377K, L407A, L407G, or any combination thereof.

In one embodiment, the invention relates to a variant polynucleotide encoding a polypeptide having lipase activity that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence as set forth in SEQ ID NO:1, wherein the amino acid sequence of SEQ ID NO:1 comprises at least one substitution selected from K14E, F56C, K64V, K64T, K64E, P67L, W79F, W79I, K145W, K145E, E263L, I265T, I265L, Y266L, Y266V, N272P, R273Q, Y275F, N291A, N291L, N291F, A293V, F297L, M298F, A303Q, S307L, L308S, L308N, T310Q, Y340F, Y347K, V375G, Q377K, L407A, L407G.

In one embodiment, the invention relates to a variant polynucleotide encoding a polypeptide having lipase activity that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence as set forth in SEQ ID NO:1, wherein the amino acid sequence of SEQ ID NO:1 comprises more than one substitution selected from K14E, F56C, K64V, K64T, K64E, P67L, W79F, W79I, K145W, K145E, E263L, I265T, I265L, Y266L, Y266V, N272P, R273Q, Y275F, N291A, N291L, N291F, A293V, F297L, M298F, A303Q, S307L, L308S, L308N, T310Q, Y340F, Y347K, V375G, Q377K, L407A, L407G. The amino acid sequence of SEQ ID NO:1 may comprise a combination selected from (a1) N291A, 405L; (b1) W79F, I265L, N291L; (c1) E263L, T310Q; (d1) T310Q, L407A; (e1) K145E, L407A; (f1) K64V, L407A; (g1) M298F, L407A; (h1) K145E, Y340F; (i1) T310Q, L407A; (j1) T310Q, L407A; (k1) K14E, K64V, K145E, T310Q, L407A; (l1) K64V, K145E, M298F, T310Q, L407A; (m1) E263L, F297L, T310Q, L407A; (n1) E263L, F297L, T310Q, L407G; (o1) P67L, E263L, F297L, T310Q; (p1) F297L, T310Q; (q1) E263L, F297L; (r1) E263L, Q377K, T310Q, L407A; (s1) E263L, Q377K, T310Q, L407G; (t1) K14E, E2363L, I265T, A303Q, T310Q; (u1) E263L, T310Q, L407A; (v1) E263L, T310Q, L407G; (w1) E263L, M298F, T310Q; (x1) K145E, E263L, A303Q, T310Q, L407A; (y1) K145E, E263L, A303Q, T310Q, L407G; (z1) K64V, K145E, E263L, A303Q, T310Q; (a2) K145E, E263L, A303Q; (b2) K145E, A303Q; (c2) K145E, Y340F, Y347K, L407A; (d2) K145E, T310Q; (e2) K145E, E263L; (f2) K145E, Y347K; (g2) K145E, K64V; (h2) K145E, Y266L, A303Q; (i2) K145E, E263L, M298F, T310Q, L407A; (j2) K145E, E263L, M298F, T310Q, L407G; (k2) K145E, E263L, T310Q, L407A; (l2) K145E, E263L, T310Q, L407G; (m2) K14E, A303Q, L407A; (n2) K14E, E263L, A303Q, T310Q, L407A; (o2) K145W, E263L, I265T, A303Q, T310Q, L407A; (p2) K145W, I265T, A303Q, L407A; (q2) K64V, K145W, E263L, T310Q, L407A; (r2) K64V, K145W, E263L, M298F, T310Q; (s2) K64V, K145W, E263L, Y266L, T310Q; (t2) A303Q, L407A; (u2) M298F, L407G; (v2) I265T, M298F, L407A; (w2) I265T, M298F, L407G; (x2) Y266L, M298F, L407A; (y2) Y266L, M298F, L407G; (z2) P67L, F297L, L407A; (a3) P67L, F297L, L407G; (b3) I265T, L407A; (c3) Y266L, L407G; (d3) E263L, L407A; (e3) K145E, Y340F; (f3) K145E, Y340F; (g3) K145E, Y340F; (h3) K14E, A303Q, L407A; (i3) K14E, A303Q, L407A; (j3) K14E, A303Q, L407A; and (k3) K14E, K64V, K145E, M298F, T310Q, L407A.

The polynucleotide of the invention in one aspect encodes a variant polypeptide having lipase activity, wherein the variant polypeptide is an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence as set forth in SEQ ID NO:1, wherein the variant polypeptide exerts increased enzymatic activity, pH-stability, stability against proteolytic degradation, or any combination thereof when compared to the lipase of SEQ ID NO:1.

The variant polynucleotide of the invention in one aspect encodes a polypeptide having lipase activity comprising an amino acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence of SEQ ID NO:1 has an increase in at least one characteristic selected from enzyme activity, pH-stability, stability against proteolytic degradation and stability in detergent formulation, and any combination thereof when compared to a *Thermomyces lanuginosa* lipase according to amino acids 1-269 of SEQ ID NO: 2 of U.S. Pat. No. 5,869,438 and/or when compared to a *Thermomyces lanuginosa* lipase according to amino acids 1-269 of SEQ ID NO: 2 of U.S. Pat. No. 5,869,438 with amino acid substitutions T231R and N233R.

In one embodiment, the invention relates to a polynucleotide encoding a polypeptide having lipase activity, wherein the polypeptide is a fragment of the inventive full length amino acid sequence as disclosed above.

In one embodiment, the invention relates to a polynucleotide encoding a polypeptide having lipase activity, wherein the polypeptide is a hybrid of at least one inventive polypeptide and at least one polypeptide different from the inventive polypeptide. In one embodiment, the polynucleotide encodes a polypeptide having lipase activity, wherein the polypeptide is a hybrid of at least one inventive polypeptide and at least one lipase different from the inventive polypeptide.

Variant polynucleotide and variant polypeptide sequences may be defined by their "sequence identity" when compared to a parent sequence. Sequence identity usually is provided as "% sequence identity" or "% identity". For calculation of sequence identities, in a first step a sequence alignment has to be produced. According to this invention, a pairwise global alignment has to be produced, meaning that two sequences have to be aligned over their complete length, which is usually produced by using a mathematical approach, called alignment algorithm.

According to the invention, the alignment is generated by using the algorithm of Needleman and Wunsch (J. Mol. Biol. (1979) 48, p. 443-453). Preferably, the program "NEEDLE" (The European Molecular Biology Open Software Suite (EMBOSS)) is used for the purposes of the current invention, with using the programs default parameter (polynucleotides: gap open=10.0, gap extend=0.5 and matrix=EDNAFULL; polypeptides: gap open=10.0, gap extend=0.5 and matrix=EBLOSUM62).

After aligning two sequences, in a second step, an identity value is determined from the alignment produced.

In one embodiment, the %-identity is calculated by dividing the number of identical residues by the length of the alignment region which is showing the respective sequence of this invention over its complete length multiplied with 100: %-identity=(identical residues/length of the alignment region which is showing the respective sequence of this invention over its complete length)*100.

In a preferred embodiment, the %-identity is calculated by dividing the number of identical residues by the length of the alignment region which is showing the two aligned sequences over their complete length multiplied with 100:

%-identity=(identical residues/length of the alignment region which is showing the two aligned sequences over their complete length)*100.

Variant polypeptides may be defined by their "sequence similarity" when compared to a parent sequence. Sequence similarity usually is provided as "% sequence similarity" or "%-similarity". % sequence similarity takes into account that defined sets of amino acids share similar properties, e.g by their size, by their hydrophobicity, by their charge, or by other characteristics. Herein, the exchange of one amino acid with a similar amino acid may be called "conservative mutation". Similar amino acids according to the invention are defined as follows: amino acid A is similar to amino acids S; amino acid D is similar to amino acids E and N; amino acid E is similar to amino acids D, K, and Q; amino acid F is similar to amino acids W and Y; amino acid H is similar to amino acids N and Y; amino acid I is similar to amino acids L, M, and V; amino acid K is similar to amino acids E, Q, and R; amino acid L is similar to amino acids I, M, and V; amino acid M is similar to amino acids I, L, and V; amino acid N is similar to amino acids D, H, and S; amino acid Q is similar to amino acids E, K, and R; amino acid R is similar to amino acids K and Q; amino acid S is similar to amino acids A, N, and T; amino acid T is similar to amino acids S; amino acid V is similar to amino acids I, L, and M; amino acid W is similar to amino acids F and Y; amino acid Y is similar to amino acids F, H, and W.

Conservative amino acid substitutions may occur over the full length of the sequence of a polypeptide sequence of a functional protein such as an enzyme. In one embodiment, such mutations are not pertaining the functional domains of an enzyme. In one embodiment, conservative mutations are not pertaining the catalytic centers of an enzyme.

For calculation of sequence similarity is, in a first step a sequence alignment has to be produced as described above.

In one embodiment, the %-similarity is calculated by dividing the number of identical residues plus the number of similar residues by the length of the alignment region which is showing the respective sequence of this invention over its complete length multiplied with 100: %-similarity=[(identical residues+similar residues)/length of the alignment region which is showing the respective sequence of this invention over its complete length]*100.

In a preferred embodiment, the %-similarity is calculated by dividing the number of identical residues plus the number of similar residues by the length of the alignment region which is showing the two aligned sequences over their complete length multiplied with 100: %-similarity=[(identical residues+similar residues)/length of the alignment region which is showing the two aligned sequences over their complete length]*100.

A polynucleotide encoding a polypeptide may be "expressed". "Expression" usually describes the process undergone by a polynucleotide sequence encoding a polypeptide to actually produce said polypeptide in an organism.

Industrial production of enzymes usually is done by using expression systems. "Wild-type cells" herein means cells prior to a certain modification. The term "recombinant cell" (also called "genetically modified cell" herein) refers to a cell which has been genetically altered, modified or engineered such that it exhibits an altered, modified or different genotype as compared to the wild-type cell which it was derived from. The "recombinant cell" may comprise an exogenous polynucleotide encoding a certain protein or enzyme and therefore may express said protein or enzyme.

"Expression system" may mean a host microorganism, expression hosts, host cell, production organism, or production strain and each of these terms can be used interchangeably. Examples of expression systems include but are not limited to: *Aspergillus niger*, *Aspergillus oryzae*, *Hansenula polymorpha*, *Thermomyces lanuginosus*, *Fusarium oxysporum*, *Fusarium heterosporum*, *Escherichia coli*, *Bacillus*, preferably *Bacillus subtilis*, or *Bacillus licheniformis*, *Pseudomonas*, preferably *Pseudomonas fluorescens*, *Pichia pastoris* (also known as *Komagataella phaffii*, *Myceliopthora thermophile* (C1), *Thermothelomyces thermophila*, *Schizosaccharomyces pombe*, *Trichoderma*, preferably *Trichoderma reesei* and *Saccharomyces*, preferably *Saccharomyces cerevisiae*. The variant polypeptides are produced using the expression system listed above.

The term "non-naturally occurring" refers to a (poly) nucleotide, amino acid, (poly)peptide, enzyme, protein, cell, organism, or other material that is not present in its original naturally occurring environment or source.

The term "heterologous" (or exogenous or foreign or recombinant) in the context of polynucleotides and polypeptides is defined herein as:
(a) not native to the host cell;
(b) native to the host cell; however, structural modifications, e.g., deletions, substitutions, and/or insertions, are included as a result of manipulation of the DNA of the host cell by recombinant DNA techniques to alter the native sequence; or
(c) native to the host cell but expression is quantitatively altered or expression is directed from a genomic location different from the native host cell as a result of manipulation of the DNA of the host cell by recombinant DNA techniques, e.g., a stronger promoter.

With respect to two or more polynucleotide sequences or two or more amino acid sequences, the term "heterologous" is used to characterize that the two or more polynucleotide sequences or two or more amino acid sequences do not occur naturally in the specific combination with each other.

"Genetic Construct" or "expression cassette" as used herein, is a DNA molecule composed of at least one sequence of interest to be expressed, operably linked to one or more control sequences (at least to a promoter) as described herein. Typically, the expression cassette comprises three elements: a promoter sequence, an open reading frame, and a 3' untranslated region that, in eukaryotes, usually contains a polyadenylation site. Additional regulatory elements may include transcriptional as well as translational enhancers. An intron sequence may also be added to the 5' untranslated region (UTR) or in the coding sequence to increase the amount of the mature message that accumulates in the cytosol. The expression cassette may be part of a vector or may be integrated into the genome of a host cell and replicated together with the genome of its host cell. The expression cassette usually is capable of increasing or decreasing expression.

The term "vector" as used herein comprises any kind of construct suitable to carry foreign polynucleotide sequences for transfer to another cell, or for stable or transient expression within a given cell. The term "vector" as used herein encompasses any kind of cloning vehicles, such as but not limited to plasmids, phagemids, viral vectors (e.g., phages), bacteriophage, baculoviruses, cosmids, fosmids, artificial chromosomes, or and any other vectors specific for specific hosts of interest. Low copy number or high copy number vectors are also included. Foreign polynucleotide sequences usually comprise a coding sequence which may be referred to herein as "gene of interest". The gene of interest may comprise introns and exons, depending on the kind of origin or destination of host cell.

A vector as used herein may provide segments for transcription and translation of a foreign polynucleotide upon transformation into a host cell or host cell organelles. Such additional segments may include regulatory nucleotide sequences, one or more origins of replication that is required for its maintenance and/or replication in a specific cell type, one or more selectable markers, a polyadenylation signal, a suitable site for the insertion of foreign coding sequences such as a multiple cloning site etc. One example is when a vector is required to be maintained in a bacterial cell as an episomal genetic element (e.g. plasmid or cosmid molecule). Non-limiting examples of suitable origins of replication include the f1-ori and colE1.

A vector may replicate without integrating into the genome of a host cell, e.g. as a plasmid in a bacterial host cell, or it may integrate part or all of its DNA into the genome of the host cell and thus lead to replication and expression of its DNA.

Foreign nucleic acid may be introduced into a vector by means of cloning. Cloning may mean that by cleavage of the vector (e.g. within the multiple cloning site) and the foreign polynucleotide by suitable means and methods (e.g., restriction enzymes), fitting structures within the individual nucleic acids may be created that enable the controlled fusion of said foreign nucleic acid and the vector.

Once introduced into the vector, the foreign nucleic acid comprising a coding sequence may be suitable to be introduced (transformed, transduced, transfected, etc.) into a host cell or host cell organelles. A cloning vector may be chosen suitable for expression of the foreign polynucleotide sequence in the host cell or host cell organelles.

The term "introduction" or "transformation" as referred to herein encompasses the transfer of an exogenous polynucleotide into a host cell, irrespective of the method used for transfer. That is, the term "transformation" as used herein is independent from vector, shuttle system, or host cell, and it not only relates to the polynucleotide transfer method of transformation as known in the art (cf., for example, Sambrook, J. et al. (1989) Molecular Cloning: A Laboratory Manual, 2nd Ed., Cold Spring Harbor Laboratory Press, Cold Spring Harbor, N.Y.), but it encompasses any further kind polynucleotide transfer methods such as, but not limited to, transduction or transfection. Plant tissue capable of subsequent clonal propagation, whether by organogenesis or embryogenesis, may be transformed with a genetic construct and a whole plant regenerated therefrom. The particular tissue chosen will vary depending on the clonal propagation systems available for, and best suited to, the particular species being transformed.

In one embodiment of the invention, a vector is used for transformation of a host cell.

The polynucleotide may be transiently or stably introduced into a host cell and may be maintained non-integrated, for example, as a plasmid. "Stable transformation" may mean that the transformed cell or cell organelle passes the nucleic acid comprising the foreign coding sequence on to the next generations of the cell or cell organelles. Usually stable transformation is due to integration of nucleic acid comprising a foreign coding sequence into the chromosomes or as an episome (separate piece of nuclear DNA).

"Transient transformation" may mean that the cell or cell organelle once transformed expresses the foreign nucleic acid sequence for a certain time—mostly within one generation. Usually transient transformation is due to nucleic acid comprising a foreign nucleic acid sequence is not integrated into the chromosomes or as an episome.

Alternatively, it may be integrated into the host genome. The resulting transformed plant cell may then be used to regenerate a transformed plant in a manner known to persons skilled in the art.

Recombinant cells may exhibit "increased" or "decreased" expression when compared to the respective wild-type cell.

The term "increased expression", "enhanced expression" or "overexpression" as used herein means any form of expression that is additional to the original wild-type expression level (which can be absence of expression or immeasurable expression as well). Reference herein to "increased expression", "enhanced expression" or "overexpression" is taken to mean an increase in gene expression and/or, as far as referring to polypeptides, increased polypeptide levels and/or increased polypeptide activity, relative to control organisms. The increase in expression may be in increasing order of preference at least 5%, at least 10%, at least 20%, at least 30%, at least 40%, at least 50%, at least 60%, at least 70%, at least 80%, at least 85%, at least 90%, or 100% or even more compared to that of control organisms.

Methods for increasing expression of genes or gene products, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to increase expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO 93/22443), or isolated promoters may be introduced into an organism in the proper orientation and distance from a gene of the present invention so as to control the expression of the gene.

An intron sequence may also be added to the 5' untranslated region (UTR) or the coding sequence of the partial coding sequence to increase the amount of the mature message that accumulates in the cytosol. Inclusion of a spliceable intron in the transcription unit in expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit.

To obtain increased expression or overexpression of a polypeptide most commonly the nucleic acid encoding this polypeptide is overexpressed in sense orientation with a polyadenylation signal. Introns or other enhancing elements may be used in addition to a promoter suitable for driving expression with the intended expression pattern.

Enzymes are generally produced commercially by using recombinant cells which express the desired enzyme by cultivation of the same under conditions suitable for expression of the desired enzyme.

Cultivation normally takes place in a suitable nutrient medium allowing the recombinant cells to grow (this process may be called fermentation) and express the desired protein. At the end of fermentation, fermentation broth is collected and may be further processed, wherein the fermentation broth comprises a liquid fraction and a solid fraction.

The enzyme of interest may be secreted (into the liquid fraction of the fermentation broth) or may not be secreted from the host cells (and therefore is comprised in the cells of the fermentation broth). Depending on this, the desired protein or enzyme may be recovered from the liquid fraction of the fermentation broth or from cell lysates. Recovery of the desired enzyme uses methods known to those skilled in the art. Suitable methods for recovery of proteins or enzymes from fermentation broth include but are not limited to collection, centrifugation, filtration, extraction, and precipitation. If the enzyme of interest precipitates or crystallizes in the fermentation broth or binds at least in part to the particulate matter of the fermentation broth additional treatment steps might be needed to release the enzyme from the biomass or solubilize enzyme crystals and precipitates. U.S. Pat. No. 6,316,240B1 describes a method for recovering an enzyme, which precipitates and/or crystallizes during fermentation, from the fermentation broth. In case the desired enzyme is comprised in the cells of the fermentation broth release of the enzyme from the cells might be needed. Release from the cells can be achieved for instance, but not being limited thereto, by cell lysis with techniques well known to the skilled person.

The enzyme of interest may be further purified from the fermentation broth. The resulting product may be called "isolated polypeptide product" herein or "isolated lipase product", wherein the polypeptide or lipase in this context means the polypeptide or lipase of the invention. The term "purification" or "purifying" refers to a process in which at least one component, e.g., a protein of interest, is separated from at least another component, e.g., a particulate matter of a fermentation broth, and transferred into a different compartment or phase, wherein the different compartments or phases do not necessarily need to be separated by a physical barrier. Examples of such different compartments are two compartments separated by a filtration membrane or cloth, i.e., filtrate and retentate; examples of such different phases are pellet and supernatant or cake and filtrate, respectively.

"Pure polypeptide having lipase activity" means that the polypeptide of the invention is comprised in the isolated polypeptide product in amounts of at least about 80% by weight, relative to the total weight of the isolated polypeptide product. "Pure polypeptide having lipase activity" may mean that the polypeptide of the invention is comprised in the isolated polypeptide product in amounts of at least about 81% by weight, at least about 82% by weight, at least about 83% by weight, at least about 84% by weight, at least about 85% by weight, at least about 86% by weight, at least about 87% by weight, at least about 88% by weight, at least about 89% by weight, at least about 90% by weight, at least about 91% by weight, at least about 92% by weight, at least about 93% by weight, at least about 94% by weight, at least about 95% by weight, at least about 96% by weight, at least about 97% by weight, at least about 98% by weight, at least about 99% by weight, or 100% by weight, all relative to the total weight of the polypeptide product. Preferably "purified" means that the material is in a 100% pure state. "Pure polypeptide having lipase activity" may mean that the amount of compounds different from the polypeptide of the invention comprised in the isolated polypeptide product is less than 20% by weight, less than 19% by weight, less than 18% by weight, less than 17% by weight, less than 16% by weight, less than 15% by weight, less than 14% by weight, less than 13% by weight, less than 12% by weight, less than 11% by weight, less than 10% by weight, less than 9% by weight, less than 8% by weight, less than 7% by weight, less than 6% by weight, less than 5% by weight, less than 4% by weight, less than 3% by weight, less than 2% by weight, or less than 1% by weight, all relative to the total weight of the polypeptide product. Compounds different from the polypeptide of the invention comprised in the isolated polypeptide product may be e.g. components such as salts originating from the fermentation medium, cell debris originating from the production host cells, metabolites produced by the production host cells during fermentation.

The enzyme produced by fermentation and purified to a certain extent may be in liquid form. "Liquid" is related to the physical appearance at 20° C. and 101.3 kPa.

The isolated polypeptide product may be further processed to form an "enzyme formulation".

"Enzyme formulation" means any non-complex formulation comprising a small number of ingredients, wherein the ingredients serve the purpose of stabilizing the enzymes comprised in the enzyme formulation and/or the stabilization of the enzyme formulation itself. The term "enzyme stability" relates to the retention of enzymatic activity as a function of time during storage or operation. The term "enzyme formulation stability" relates to the maintenance of physical appearance of the enzyme formulation during storage or operation as well as the avoidance of microbial contamination during storage or operation.

An "enzyme formulation" is a composition which is meant to be formulated into a complex formulation which itself may be determined for final use. An "enzyme formulation" according to the invention is not a complex formulation comprising several components, wherein the components are formulated into the complex formulation to exert each individually a specific action in a final application. A complex formulation may be without being limited thereto a detergent formulation, wherein individual detergent components are formulated in amounts effective in the washing performance of the detergent formulation.

In one aspect of the invention, at least one amylase variant of the invention is comprised in an enzyme formulation.

The enzyme formulation can be either solid or liquid. Enzyme formulations can be obtained by using techniques known in the art. For instance, without being limited thereto, solid enzyme formulations can be obtained by extrusion or granulation. Suitable extrusion and granulation techniques are known in the art and are described for instance in WO 94/19444A1 and WO 97/43482A1.

Liquid enzyme formulations may comprise amounts of enzyme in the range of 0.1% to 40% by weight, or 0.5% to 30% by weight, or 1% to 25% by weight, or 3% to 10% by weight, all relative to the total weight of the enzyme concentrate.

The liquid enzyme formulation may comprise more than one type of enzyme. In one embodiment, the enzyme formulation comprises one or more lipases according to the present invention. In one embodiment, the enzyme formulation comprises one or more lipases according to the present invention and at least one additional enzyme selected from the group of a lipase different from the inventive lipases, a protease, a cellulase, an amylase, a laccase, a pectinase, a nuclease, and any combination thereof. Aqueous enzyme formulations of the invention may comprise water in amounts of more than about 50% by weight, more than about 60% by weight, more than about 70% by weight, or more than about 80% by weight, all relative to the total weight of the enzyme formulation.

In one embodiment, the enzyme formulation comprises in addition to at least one polypeptide of the invention one or more compounds selected from the group consisting of other enzymes, preservatives and stabilizers.

In one embodiment, a liquid enzyme formulation comprises at least one polypeptide variant of the invention and at least one preservative. Non-limiting examples of suitable preservatives include (quaternary) ammonium compounds, isothiazolinones, organic acids, and formaldehyde releasing agents. Non-limiting examples of suitable (quaternary) ammonium compounds include benzalkonium chlorides, polyhexamethylene biguanide (PHMB), Didecyldimethylammonium chloride (DDAC), and N-(3-aminopropyl)-N-dodecylpropane-1,3-diamine (Diamine). Non-limiting examples of suitable isothiazolinones include 1,2-benzisothiazolin-3-one (BIT), 2-methyl-2H-isothiazol-3-one (MIT), 5-chloro-2-methyl-2H-isothiazol-3-one (CIT), 2-octyl-2H-isothiazol-3-one (O1T), and 2-butyl-benzo[d]isothiazol-3-one (BBIT). Non-limiting examples of suitable organic acids include benzoic acid, sorbic acid, L-(+)-lactic acid, formic acid, and salicylic acid. Non-limiting examples of suitable formaldehyde releasing agent include N,N'-methylenebismorpho-line (MBM), 2,2',2"-(hexahydro-1,3,5-triazine-1,3,5-triyl)triethanol (HHT), (ethylenedioxy)di-methanol, .alpha., .alpha.', .alpha."-trimethyl-1,3,5-triazine-1,3,5 (2H,4H,6H)-triethanol (HPT), 3,3'-methylenebis[5-methyloxazolidine] (MBO), and cis-1-(3-chloroallyl)-3,5,7-triaza-1-azoniaadamantane chloride (CTAC).

Further useful preservatives include iodopropynyl butylcarbamate (IPBC), halogen releasing compounds such as dichloro-dimethyl-hydantoine (DCDMH), bromo-chloro-dimethyl-hydantoine (BCDMH), and dibromo-dimethyl-hydantoine (DBDMH); bromo-nitro compounds such as Bronopol (2-bromo-2-nitropropane-1,3-diol), 2,2-dibromo-2-cyanoacetamide (DBNPA); aldehydes such as glutaraldehyde; phenoxyethanol; Biphenyl-2-ol; and zinc or sodium pyrithione.

In one embodiment, a liquid enzyme formulation comprises at least one polypeptide variant of the invention and at least one enzyme stabilizer. An enzyme stabilizer is selected from substances which are capable of reducing loss of enzymatic activity during storage of at least one enzyme comprised in a liquid enzyme concentrate. Reduced loss of enzymatic activity within this invention may mean that the loss of enzymatic activity is reduced by at least 5%, by at least 10%, by at least 15%, by at least 20%, by at least 25%, by at least 30%, by at least 40%, by at least 50%, by least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% when compared to the initial enzymatic activity before storage.

In one embodiment, at least one enzyme stabilizer is selected from lipase stabilizing compounds. A lipase is stable according to the invention, when its lipolytic activity "available in application" equals 100% when compared to the initial lipolytic activity before storage. A lipase may be called stable within this invention if its lipolytic activity available in application is at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% when compared to the initial lipolytic activity before storage.

Lipase may be stabilized in the presence of at least one compound selected from salts like NaCl or KCl, or alkali salts of lactic acid and formic acid.

The invention relates to a combination of at least one variant polypeptide of the invention and at least one other enzyme. In one aspect, such a combination is part of a liquid enzyme formulation at 20° C. and 101.3 kPa.

The combination of enzymes can be of the same class, for example a composition comprising a first lipase and a second lipase. Combinations of enzymes can be from a different class of enzymes, for example, a composition comprising a lipase and an amylase. Combinations of enzymes may comprise at least one variant lipase of the invention and one other enzyme. Combinations may comprise three enzymes, four enzymes, or more than four enzymes.

"Other enzyme" means any enzyme different from the lipase variants of the invention. At least one "other enzyme" may be selected from lipases, amylases, proteases, cellulases, mannanases, pectate lyases and nucleases.

At least one enzyme may be selected from the group of lipases which are different from the inventive polypeptides. "Lipases", "lipolytic enzyme", "lipid esterase", all refer to an enzyme of EC class 3.1.1 ("carboxylic ester hydrolase"). Lipases (E.C. 3.1.1.3, Triacylglycerol lipase) usually hydrolyze triglycerides to more hydrophilic mono- and diglycerides, free fatty acids, and glycerol. Lipase enzymes usually includes also enzymes which are active on substrates different from triglycerides or cleave specific fatty acids, such as Phospholipase A (E.C. 3.1.1.4), Galactolipase (E.C. 3.1.1.26), cutinase (EC 3.1.1.74), and enzymes having sterol esterase activity (EC 3.1.1.13) and/or wax-ester hydrolase activity (EC 3.1.1.50).

Many lipase enzymes have been described in patents and published patent applications including, but not limited to: WO 2000/032758, WO 2003/089620, WO 2005/032496, WO 2005/086900, WO 2006/00976, WO 2006/031699, WO 2008/036863, WO 2011/046812, and WO 2014/059360.

Lipases are used in detergent and cleaning products to remove grease, fat, oil, and dairy stains.

In one embodiment, lipase is selected from fungal triacylglycerol lipase (EC class 3.1.1.3). Fungal triacylglycerol lipase may be selected from lipases of *Thermomyces lanuginosa* such as triacylglycerol lipase according to amino acids 1-269 of SEQ ID NO: 2 of U.S. Pat. No. 5,869,438 (may be called Lipolase herein) and variants thereof having lipolytic activity.

Variants of *Thermomyces lanuginosa* lipase according to amino acids 1-269 of SEQ ID NO: 2 of U.S. Pat. No. 5,869,438 may be selected from variants having lipolytic activity which are at least 90%, at least 91%, at least 92%, at least 93%, at least 94%, at least 95%, at least 96%, at least 97%, at least 98% or at least 99% identical or similar when compared to the full length polypeptide sequence of amino acids 1-269 of SEQ ID NO: 2 of U.S. Pat. No. 5,869,438. The variants may be selected from polypeptide sequences being at least 90%, at least 91%, at least 92%, at least 93%, at least 94%, at least 95%, at least 96%, at least 97%, at least 98% or at least 99% identical or similar when compared to the full length polypeptide sequence of amino acids 1-269 of SEQ ID NO: 2 of U.S. Pat. No. 5,869,438.

*Thermomyces lanuginosa* lipase may be selected from variants selected from polypeptide sequences being at least 90%, at least 91%, at least 92%, at least 93%, at least 94%, at least 95%, at least 96%, at least 97%, at least 98% or at least 99% identical or similar when compared to the full length polypeptide sequence of amino acids 1-269 of SEQ ID NO: 2 of U.S. Pat. No. 5,869,438 having lipolytic activity comprising at least the following amino acid substitutions when compared to amino acids 1-269 of SEQ ID NO: 2 of U.S. Pat. No. 5,869,438: T231R and N233R (enzyme having amino acids 1-269 of SEQ ID NO: 2 of U.S. Pat. No. 5,869,438 T231R and N233R may be called Letra Lip herein). Said lipase variants may further comprise one or more of the following amino acid exchanges when compared to amino acids 1-269 of SEQ ID NO: 2 of U.S. Pat. No. 5,869,438: Q4V, V60S, A150G, L227G, P256K.

At least one enzyme may be selected from the group of amylases. Alpha-amylase (E.C. 3.2.1.1) enzymes usually perform endohydrolysis of (1→4)-alpha-D-glu-cosidic linkages in polysaccharides containing three or more (1→4)-alpha-linked D-glucose units. Amylase enzymes act on starch, glycogen and related polysaccharides and oligosaccharides in a random manner; reducing groups are liberated in the alpha-configuration. Other examples of amylase enzymes include Beta-amylase (E.C. 3.2.1.2), Glucan 1,4-alpha-maltotetraohydrolase (E.C. 3.2.1.60), Isoamylase (E.C. 3.2.1.68), Glucan 1,4-alpha-maltohexaosidase (E.C. 3.2.1.98), and Glucan 1,4-alpha-maltohydrolase (E.C. 3.2.1.133).

Many amylase enzymes have been described in patents and published patent applications including, but not limited to: WO 2002/068589, WO 2002/068597, WO 2003/083054, WO 2004/091544, and WO 2008/080093.

Amylases are known to derived from *Bacillus licheniformis* having SEQ ID NO:2 as described in WO 95/10603. Suitable variants are those which are at least 90% identical or similar to SEQ ID NO: 2 as described in WO 95/10603 and/or comprising one or more substitutions in the following positions: 15, 23, 105, 106, 124, 128, 133, 154, 156, 178, 179, 181, 188, 190, 197, 201, 202, 207, 208, 209, 211, 243, 264, 304, 305, 391, 408, and 444 which have amylolytic activity. Such variants are described in WO 94/02597, WO 94/018314, WO 97/043424 and SEQ ID NO:4 of WO 99/019467.

Amylases are known to be derived from *B. stearothermophilus* having SEQ ID NO:6 as described in WO 02/10355 or an amylase which is at least 90% identical or similar thereto having amylolytic activity. Suitable variants of SEQ ID NO:6 include those which is at least 90% identical or similar thereto and/or further comprise a deletion in positions 181 and/or 182 and/or a substitution in position 193.

Amylases are known to be derived from *Bacillus* sp. 707 having SEQ ID NO:6 as disclosed in WO 99/19467 or an amylase which is at least 90% identical or similar thereto having amylolytic activity.

Amylases are known from *Bacillus halmapalus* having SEQ ID NO:2 or SEQ ID NO:7 as described in WO 96/23872, also described as SP-722, or an amylase which is at least 90% identical or similar to one of the sequences which has amylolytic activity.

Amylases are known to be derived from *Bacillus* sp. DSM 12649 having SEQ ID NO:4 as disclosed in WO 00/22103 or an amylase which is at least 90% identical or similar thereto having amylolytic activity.

Amylases are known to be derived from *Bacillus* strain TS-23 having SEQ ID NO:2 as disclosed in WO 2009/061380 or an amylase which is at least 90% identical or similar thereto having amylolytic activity.

Amylases are known from *Cytophaga* sp. having SEQ ID NO:1 as disclosed in WO 2013/184577 or an amylase which is at least 90% identical or similar thereto having amylolytic activity.

Amylases are known from *Bacillus megaterium* DSM 90 having SEQ ID NO:1 as disclosed in WO 2010/104675 or an amylase which is at least 90% identical or similar thereto having amylolytic activity.

Amylases are known having amino acids 1 to 485 of SEQ ID NO:2 as described in WO 00/60060 or amylases comprising an amino acid sequence which is at least 96% identical or similar with amino acids 1 to 485 of SEQ ID NO:2 which have amylolytic activity.

Amylases are also known having SEQ ID NO: 12 as described in WO 2006/002643 or amylases having at least 80% identity thereto and have amylolytic activity. Suitable amylases include those having at least 80% identity compared to SEQ ID NO:12 and/or comprising the substitutions at positions Y295F and M202LITV and have amylolytic activity.

Amylases are also known having SEQ ID NO:6 as described in WO 2011/098531 or amylases having at least 80% identity thereto having amylolytic activity. Suitable amylases include those having at least 80% identity compared to SEQ ID NO:6 and/or comprising a substitution at one or more positions selected from the group consisting of 193 [G,A,S,T or M], 195 [F,W,Y,L,I or V], 197 [F,W,Y,L,I or V], 198 [Q or N], 200 [F,W,Y,L,I or V], 203 [F,W,Y,L,I or V], 206 [F,W,Y,N,L,I,V,H,Q,D or E], 210 [F,W,Y,L,I or V], 212 [F,W,Y,L,I or V], 213 [G,A,S,T or M] and 243 [F,W,Y,L,I or V] and have amylolytic activity.

Amylases are known having SEQ ID NO:1 as described in WO 2013/001078 or amylases having at least 85% identity thereto having amylolytic activity. Suitable amylases include those having at least 85% identity compared to SEQ ID NO:1 and/or comprising an alteration at two or more (several) positions corresponding to positions G304, W140, W189, D134, E260, F262, W284, W347, W439, W469, G476, and G477 and having amylolytic activity.

Amylases are known having SEQ ID NO:2 as described in WO 2013/001087 or amylases having at least 85% identity thereto and having amylolytic activity. Suitable amylases include those having at least 85% identity compared to SEQ ID NO:2 and/or comprising a deletion of positions 181+182, or 182+183, or 183+184, which have amylolytic activity. Suitable amylases include those having at least 85% identity compared to SEQ ID NO:2 and/or comprising a deletion of positions 181+182, or 182+183, or 183+184, which comprise one or two or more modifications in any of positions corresponding to W140, W159, W167, Q169, W189, E194, N260, F262, W284, F289, G304, G305, R320, W347, W439, W469, G476 and G477 and have amylolytic activity.

Amylases also include hybrid α-amylase from above mentioned amylases as for example as described in WO 2006/066594.

Amylases include hybrid amylases according to WO 2014/183920 with A and B domains having at least 90% identity to SEQ ID NO:2 of WO 2014/183920 and a C domain having at least 90% identity to SEQ ID NO:6 of WO 2014/183920, wherein the hybrid amylase has amylolytic activity; preferably the hybrid alpha-amylase is at least 95% identical or similar to SEQ ID NO: 23 of WO 2014/183920 and having amylolytic activity.

Amylases include hybrid amylase according to WO 2014/183921 with A and B domains having at least 75% identity to SEQ ID NO: 2, SEQ ID NO: 15, SEQ ID NO: 20, SEQ ID NO: 23, SEQ ID NO: 29, SEQ ID NO: 26, SEQ ID NO: 32, and SEQ ID NO: 39 as disclosed in WO 2014/183921 and a C domain having at least 90% identity to SEQ ID NO: 6 of WO 2014/183921, wherein the hybrid amylase has amylolytic activity; preferably, the hybrid alpha-amylase is at least 95% identical or similar to SEQ ID NO: 30 as disclosed in WO 2014/183921 and having amylolytic activity.

In one embodiment amylase variants include polypeptides with at least 40 to 100% identity or similarity, when compared to the full length polypeptide sequence of the parent enzyme as disclosed above. In one embodiment amylase variants having amylolytic activity are at least 70%, at least 75%, at least 80%, at least 85%, at least 90%, at least 91%, at least 92%, at least 93%, at least 94%, at least 95%, at least 96%, at least 97%, at least 98% or at least 99% identical or similar to the full length polypeptide sequence of the parent enzyme as disclosed above.

Amylases according to the invention have "amylolytic activity" or "amylase activity" according to the invention involves (endo)hydrolysis of glucosidic linkages in polysaccharides. α-amylase activity may be determined by assays for measurement of α-amylase activity. Examples of assays measuring α-amylase activity are: α-amylase activity can be determined by a method employing Phadebas tablets as substrate (Phadebas Amylase Test, supplied by Magle Life Science). Starch is hydrolyzed by the α-amylase giving soluble blue fragments. The absorbance of the resulting blue solution, measured spectrophotometrically at 620 nm, is a function of the α-amylase activity. The measured absorbance is directly proportional to the specific activity (activity/mg of pure α-amylase protein) of the α-amylase in question under the given set of conditions.

Alpha-amylase activity can also be determined by a method employing the Ethyliden-4-nitro-phenyl-α-D-maltoheptaosid (EPS). D-maltoheptaoside is a blocked oligosaccharide which can be cleaved by an endo-amylase. Following the cleavage, the α-glucosidase included in the kit to digest the substrate to liberate a free PNP molecule which has a yellow color and thus can be measured by visible spectophotometry at 405 nm. Kits containing EPS substrate and α-glucosidase is manufactured by Roche Costum Biotech (cat. No. 10880078103). The slope of the time dependent absorption-curve is directly proportional to the specific activity (activity per mg enzyme) of the α-amylase in question under the given set of conditions.

At least one enzyme may be selected from the group of cellulases. "Cellulases", "cellulase enzymes" or "cellulolytic enzymes" are enzymes involved in hydrolysis of cellulose. Three major types of cellulases are known, namely endo-ss-1,4-glucanase (endo-1,4-P-D-glucan 4-glucano-hydrolase, E.C. 3.2.1.4; hydrolyzing β-1,4-glucosidic bonds in cellulose), cellobiohydrolase (1,4-P-D-glucan cellobiohydrolase, EC 3.2.1.91), and ss-glucosidase (EC 3.2.1.21).

Endoglucanases may be classified by amino acid sequence similarities (Henrissat, B. Accessed at UniProt Oct. 26, 2011) under family 5 containing more than 20 endoglucanases of EC 3.2.1.4. Reference is also made to T.-M. Enveri, "Microbial Cellulases" in W.M. Fogarty, Microbial Enzymes and Biotechnology, Applied Science Publishers, p. 183-224 (1983); Methods in Enzymology, (1988) Vol. 160, p. 200-391 (edited by Wood, W. A. and Kellogg, S.T.); Beguin, P., "Molecular Biology of Cellulose Degradation", Annu. Rev. Microbiol. (1990), Vol. 44, pp. 219248; Begun, P. and Aubert, J-P., "The biological degradation of cellulose", FEMS Microbiology Reviews 13 (1994) p. 25-58; Henrissat, B., "Cellulases and their interaction with cellulose", Cellulose (1994), Vol. 1, pp. 169-196. Preferably, at least one cellulase is selected of the glycosyl hydrolase family 7 (GH7, pfam00840), preferably selected from endoglucanases (EC 3.2.1.4).

Cellulase enzymes have been described in patents and published patent applications including, but not limited to: WO 1997/025417, WO 1998/024799, WO 2003/068910, WO 2005/003319, and WO 2009/020459.

In one embodiment, at least one cellulase is selected from cellulases comprising a cellulose binding domain. In one embodiment, at least one cellulase is selected from cellulases comprising a catalytic domain only, meaning that the cellulase lacks cellulose binding domain.

In one embodiment, at least one cellulase is selected from Humicola, such as Humicola insolens (DSM1800) as disclosed in EP 0495257, EP 0531315, EP 0531372, U.S. Pat. Nos. 4,435,307, 5,648,263, 5,776,757, WO 89/09259, WO 91/17244, WO 94/07998 (sequence displayed in FIG. 1 "43kd human variants thereof), WO 95/24471, WO 96/11262 and WO 98/12307.

In one embodiment, at least one cellulase is selected from Trichoderma, such as Trichoderma reesei; Trichoderma longibrachiatum or Trichoderma harzianum as disclosed in EP 1305432, EP 1240525, WO 92/06165, WO 94/21801, WO 94/26880, WO 95/02043, WO 95/24471 and WO 02/099091.

Suitable cellulases include cellulase variants having cellulolytic activity which are at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% identical or similar when compared to the full-length polypeptide sequence of the respective parent enzyme.

Cellulases according to the invention have "cellulolytic activity" or "cellulase activity". Assays for measurement of cellulolytic activity include: cellulolytic activity may be determined by virtue of the fact that cellulase hydrolyses carboxymethyl cellulose to reducing carbohydrates, the reducing ability of which is determined colorimetrically by means of the ferricyanide reaction, according to Hoffman, W. S., J. Biol. Chem. 120, 51 (1937).

At least one enzyme may be selected from the group of mannan degrading enzyme. At least one mannan degrading enzyme may be selected from β-mannosidase (EC 3.2.1.25), endo-1,4-β-mannosidase (EC 3.2.1.78), and 1,4-β-mannobiosidase (EC 3.2.1.100). Preferably, at least one mannan degrading enzyme is selected from the group of endo-1,4-β-mannosidase (EC 3.2.1.78), a group of enzymes which may be called endo-β-1,4-D-mannanase, β-mannanase, or mannanase herein.

A polypeptide having mannan degrading activity or mannanase activity may be tested for according to standard test procedures known in the art, such as by applying a solution to be tested to 4 mm diameter holes punched out in agar plates containing 0.2% AZCL galactomannan (carob), i. e. substrate for the assay of endo-1,4-beta-D-mannanase available as CatNo. I-AZGMA from the company Megazyme (Megazyme's Internet address: http://www.megazyme.com/Purchase/index.html).

At least one mannanase may be selected from alkaline mannanase of Family 5 or 26. The term "alkaline mannanase" is meant to encompass mannanases having an enzymatic activity of at least 40% of its maximum activity at a given pH ranging from 7 to 12, preferably 7.5 to 10.5.

At least one mannanase may be selected from mannanases originating from Bacillus organisms, such as described in JP-0304706 [beta-mannanase from Bacillus sp.], JP-63056289 [alkaline, thermostable beta-mannanase], JP-63036774 [Bacillus microorganism FERM P-8856 producing beta-mannanase and beta-mannosidase at an alkaline pH], JP-08051975 [alkaline beta-mannanases from alkalophilic Bacillus sp. AM-001], WO 97/11164 [mannanase from Bacillus amyloliquefaciens], WO 91/18974 [mannanase active at an extreme pH and temperature], WO 97/11164 [mannanase from Bacillus amyloliquefaciens], WO 2014/100018 [endo-(3-mannanase1 cloned from a Bacillus circulars or Bacillus lentus strain CMG1240 (Bleman1; see U.S. Pat. No. 5,476,775)]. Suitable mannanases are described in WO 99/064619].

At least one mannanase comprised in component (b) may be selected from mannanases originating from *Trichoderma* organisms, such as disclosed in WO 93/24622 or in WO 2011/085747.

Suitable mannanases include also those, which are variants of the above described mannanases which have mannan degrading activity. In one embodiment mannanase variants include variants with at least 40 to 100% identity or similarity when compared to the full length polypeptide sequence of the parent enzyme as disclosed above. In one embodiment mannanase variants having mannan degrading activity are at least 70%, at least 75%, at least 80%, at least 85%, at least 90%, at least 91%, at least 92%, at least 93%, at least 94%, at least 95%, at least 96%, at least 97%, at least 98% or at least 99% identical or similar to the full length polypeptide sequence of the parent enzyme as disclosed above.

At least one enzyme may be selected from pectate lyases. Pectate lyase (E.C. 4.2.2.2) enzymes eliminative cleavage of (1→4)-alpha-D-galacturonan to give oligosaccharides with 4-deoxy-alpha-D-galact-4-enuronosyl groups at their non-reducing ends.

Pectate lyase enzymes have been described in patents and published patent applications including, but not limited to: WO2004/090099. Pectate lyase are known to be derived from *Bacillus*, particularly *B. licheniformis* or *B. agaradhaerens*, or a variant derived of any of these, e.g. as described in U.S. Pat. No. 6,124,127, WO 99/027083, WO 99/027084, WO 2002/006442, WO 2002/092741, WO 2003/095638.

Commercially available pectate lyase enzymes include: Xpect™, Pectawash™ and Pectaway™ (Novozymes NS); PrimaGreen™, EcoScour (DuPont).

At least one enzyme may be selected from the group of nucleases. Nuclease (EC 3.1.21.1) also known as Deoxyribonuclease I, or DNase preforms endonucleolytic cleavage to 5'-phosphodi-nucleotide and 5'-phosphooligonucleotide end-products.

Nuclease enzymes have been described in patents and published patent applications including, but not limited to: U.S. Pat. No. 3,451,935, GB 1300596, DE 10304331, WO 2015/155350, WO 2015/155351, WO 2015/166075, WO 2015/181287, and WO 2015/181286.

At least one enzyme may be selected from the group of proteases. Enzymes having proteolytic activity are called "proteases" or "peptidases". Proteases are active proteins exerting "protease activity" or "proteolytic activity".

Proteases are members of class EC 3.4, Proteases include aminopeptidases (EC 3.4.11), dipeptidases (EC 3.4.13), dipeptidyl-peptidases and tripeptidyl-peptidases (EC 3.4.14), peptidyl-dipeptidases (EC 3.4.15), serine-type carboxypeptidases (EC 3.4.16), metallocarboxypeptidases (EC 3.4.17), cysteine-type carboxypeptidases (EC 3.4.18), omega peptidases (EC 3.4.19), serine endopeptidases (EC 3.4.21), cysteine endopeptidases (EC 3.4.22), aspartic endopeptidases (EC 3.4.23), metallo-endopeptidases (EC 3.4.24), threonine endopeptidases (EC 3.4.25), endopeptidases of unknown catalytic mechanism (EC 3.4.99).

Commercially available protease enzymes include but are not limited to: Lavergy™ Pro (BASF); Alcalase®, Blaze®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes NS), those sold under the tradename Maxatase®, Maxacal®, Maxapem®, Purafect®, Purafect® Prime, Purafect MA®, Purafect Ox®, Purafect OxP®, Puramax®, Properase®, FN2®, FN3®, FN4®, Excellase®, Eraser®, Ultimase®, Opticlean®, Effectenz®, Preferenz® and Optimase® (Danisco/DuPont), Axapem™ (Gist-Brocases N.V.), *Bacillus lentus* Alkaline Protease, and KAP (*Bacillus alkalophilus* subtilisin) from Kao.

At least one protease may be selected from serine proteases (EC 3.4.21). Serine proteases or serine peptidases (EC 3.4.21) are characterized by having a serine in the catalytically active site, which forms a covalent adduct with the substrate during the catalytic reaction. A serine protease may be selected from the group consisting of chymotrypsin (e.g., EC 3.4.21.1), elastase (e.g., EC 3.4.21.36), elastase (e.g., EC 3.4.21.37 or EC 3.4.21.71), granzyme (e.g., EC 3.4.21.78 or EC 3.4.21.79), kallikrein (e.g., EC 3.4.21.34, EC 3.4.21.35, EC 3.4.21.118, or EC 3.4.21.119,) plasmin (e.g., EC 3.4.21.7), trypsin (e.g., EC 3.4.21.4), thrombin (e.g., EC 3.4.21.5,) and subtilisin (also known as subtilopeptidase, e.g., EC 3.4.21.62), the latter hereinafter also being referred to as "subtilisin".

A sub-group of the serine proteases tentatively designated subtilases has been proposed by Siezen et al. (1991), Protein Eng. 4:719-737 and Siezen et al. (1997), Protein Science 6:501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997), Protein Science 6:501-523. The subtilases may be divided into 6 sub-divisions, i.e. the subtilisin family, thermitase family, the proteinase K family, the lantibiotic peptidase family, the kexin family and the pyrolysin family.

A subgroup of the subtilases are the subtilisins which are serine proteases from the family S8 as defined by the MEROPS database (http://merops.sanger.ac.uk). Peptidase family S8 contains the serine endopeptidase subtilisin and its homologues. Most members of the peptidase family S8 are active at neutral-mildly alkali pH. Many peptidases in the family are thermostable.

Parent proteases of the subtilisin type (EC 3.4.21.62) and variants may be bacterial proteases. Said bacterial protease may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* protease, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* protease. A review of this family is provided, for example, in "Subtilases: Subtilisin-like Proteases" by R. Siezen, pages 75-95 in "Subtilisin enzymes", edited by R. Bott and C. Betzel, New York, 1996.

At least one protease may be selected from the following: subtilisin from *Bacillus amyloliquefaciens* BPN' (described by Vasantha et al. (1984) J. Bacteriol. Volume 159, p. 811-819 and JA Wells et al. (1983) in Nucleic Acids Research, Volume 11, p. 7911-7925); subtilisin from *Bacillus licheniformis* (subtilisin Carlsberg; disclosed in EL Smith et al. (1968) in J. Biol Chem, Volume 243, pp. 2184-2191, and Jacobs et al. (1985) in Nucl. Acids Res, Vol 13, p. 8913-8926); subtilisin PB92 (original sequence of the alkaline protease PB92 is described in EP 283075 A2); subtilisin 147 and/or 309 (Esperase®, Savinase®, respectively) as disclosed in WO 89/06279; subtilisin from *Bacillus lentus* as disclosed in WO 91/02792, such as from *Bacillus lentus* DSM 5483 or the variants of *Bacillus lentus* DSM 5483 as described in WO 95/23221; subtilisin from *Bacillus alcalophilus* (DSM 11233) disclosed in DE 10064983; subtilisin from *Bacillus gibsoni* i (DSM 14391) as disclosed in WO 2003/054184; subtilisin from *Bacillus* sp. (DSM 14390) disclosed in WO 2003/056017; subtilisin from *Bacillus* sp. (DSM 14392) disclosed in WO 2003/055974; subtilisin from *Bacillus gibsoni* i (DSM 14393) disclosed in WO 2003/054184; subtilisin having SEQ ID NO: 4 as described in WO 2005/063974; subtilisin having SEQ ID NO: 4 as described in WO 2005/103244; subtilisin having SEQ ID NO: 7 as described in WO 2005/103244; and subtilisin having SEQ ID NO: 2 as described in application DE 102005028295.4.

At least one subtilisin may be subtilisin 309 (which might be called Savinase® herein) as disclosed as sequence a) in Table I of WO 89/06279 or a variant which is at least 80% identical or similar thereto and has proteolytic activity.

Proteases are known as comprising the variants described in: WO 92/19729, WO 95/23221, WO 96/34946, WO 98/20115, WO 98/20116, WO 99/11768, WO 01/44452, WO 02/088340, WO 03/006602, WO 2004/03186, WO 2004/041979, WO 2007/006305, WO 2011/036263, WO 2011/036264, and WO 2011/072099. Suitable examples comprise especially protease variants of subtilisin protease derived from SEQ ID NO:22 as described in EP 1921147 (with amino acid substitutions in one or more of the following positions: 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and 274 which have proteolytic activity. In addition, a subtilisin protease is not mutated at positions Asp32, His64 and Ser221.

Suitable proteases include protease variants having proteolytic activity which are at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% identical or similar when compared to the full-length polypeptide sequence of the parent enzyme as disclosed above.

At least one subtilisin may have SEQ ID NO:22 as described in EP 1921147, or is a variant thereof which is at least 80% identical or similar SEQ ID NO:22 as described in EP 1921147 and has proteolytic activity. In one embodiment, a subtilisin is at least 80% identical or similar to SEQ ID NO:22 as described in EP 1921147 and is characterized by having amino acid glutamic acid (E), or aspartic acid (D), or asparagine (N), or glutamine (Q), or alanine (A), or glycine (G), or serine (S) at position 101 (according to BPN' numbering) and has proteolytic activity. In one embodiment, subtilisin is at least 80% identical or similar to SEQ ID NO:22 as described in EP 1921147 and is characterized by having amino acid glutamic acid (E), or aspartic acid (D), at position 101 (according to BPN' numbering) and has proteolytic activity. Such a subtilisin variant may comprise an amino acid substitution at position 101, such as R101E or R101D, alone or in combination with one or more substitutions at positions 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and/or 274 (according to BPN' numbering) and has proteolytic activity. In one embodiment, said protease comprises one or more further substitutions: (a) threonine at position 3 (3T), (b) isoleucine at position 4 (4I), (c) alanine, threonine or arginine at position 63 (63A, 63T, or 63R), (d) aspartic acid or glutamic acid at position 156 (156D or 156E), (e) proline at position 194 (194P), (f) methionine at position 199 (199M), (g) isoleucine at position 205 (205I), (h) aspartic acid, glutamic acid or glycine at position 217 (217D, 217E or 217G), (i) combinations of two or more amino acids according to (a) to (h).

A suitable subtilisin may be at least 80% identical or similar to SEQ ID NO:22 as described in EP 1921147 and is characterized by comprising one amino acid (according to (a)-(h)) or combinations according to (i) together with the amino acid 101E, 101D, 101N, 101Q, 101A, 101G, or 101S (according to BPN' numbering) and has proteolytic activity.

In one embodiment, a subtilisin is at least 80% identical or similar to SEQ ID NO:22 as described in EP 1921147 and is characterized by comprising the mutation (according to BPN' numbering) R101E, or S3T+V41+V205I, or S3T+V41+R101E+V205I or S3T+V41+V199M+V205I+L217D, and has proteolytic activity.

In another embodiment, the subtilisin comprises an amino acid sequence having at least 80% identity to SEQ ID NO:22 as described in EP 1921147 and being further characterized by comprising S3T+V41+S9R+A15T+V68A+D99S+R101S+A103S+I104V+N218D (according to the BPN' numbering) and has proteolytic activity.

A subtilisin may have an amino acid sequence being at least 80% identical or similar to SEQ ID NO:22 as described in EP 1921147 and being further characterized by comprising R101E, and one or more substitutions selected from the group consisting of S156D, L262E, Q137H, S3T, R45E,D, Q, P55N, T58W,Y,L, Q59D,M,N,T, G61 D,R, S87E, G97S, A98D,E,R, S106A,W, N117E, H120V,D,K,N, S125M, P129D, E136Q, S144W, S161T, S163A,G, Y171 L, A172S, N185Q, V199M, Y209W, M222Q, N238H, V244T, N261T,D and L262N,Q,D (as described in WO 2016/096711 and according to the BPN' numbering), and has proteolytic activity.

Proteases according to the invention have proteolytic activity. The methods for determining proteolytic activity are well-known in the literature (see e.g. Gupta et al. (2002), Appl. Microbiol. Biotechnol. 60: 381-395). Proteolytic activity may be determined by using Succinyl-Ala-Ala-Pro-Phe-p-nitroanilide (Suc-AAPF-pNA, short AAPF; see e.g. DelMar et al. (1979), Analytical Biochem 99, 316-320) as substrate. pNA is cleaved from the substrate molecule by proteolytic cleavage, resulting in release of yellow color of free pNA which can be quantified by measuring OD405.

In one aspect of the invention, the polypeptide according to an amino acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence of SEQ ID NO:1 having lipase activity is provided in combination with at least one protease, preferably selected from subtilisins. At least one subtilisin may be selected from those as described herein. In one embodiment, the polypeptide comprising an amino acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence of SEQ ID NO:1 having lipase activity has increased stability against proteolytic degradation in the presence of a protease, preferably in the presence of a subtilisin, when compared to a *Thermomyces lanuginosa* lipase. In one embodiment, the polypeptide comprising an amino acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence of SEQ ID NO:1 having lipase activity has increased stability against proteolytic degradation in the presence of a protease, preferably in the presence of a subtilisin, when compared to a lipase according to SEQ ID NO:1. At least one protease, preferably subtilisin, may itself be stabilized by a protease stabilizer or the protease may be non-stabilized.

In one aspect of the invention, at least one lipase variant of the invention is provided in combination with at least one subtilisin. In one embodiment, a lipase variant of the invention is stable against proteolytic degradation. In one embodiment, a lipase variant of the invention has increased stability against proteolytic degradation in the presence of a protease, preferably in the presence of a subtilisin, when compared to the respective lipase parent.

In one embodiment, at least one subtilisin is selected from subtilisin 309 as disclosed as sequence a) in Table I of WO 89/06279 or a variant thereof which is at least 80% identical or similar thereto and has proteolytic activity.

In one embodiment, subtilisin is selected from SEQ ID NO: 22 as described in EP1921147 and variants thereof having proteolytic activity. The variant of SEQ ID NO: 22 as described in EP1921147 may be a polypeptide sequence which is at least 80% identical or similar SEQ ID NO:22 as described in EP 1921147 and has proteolytic activity. In one embodiment, a subtilisin is at least 80% identical or similar to SEQ ID NO:22 as described in EP 1921147 and is characterized by having amino acid glutamic acid (E), or aspartic acid (D), or asparagine (N), or glutamine (Q), or alanine (A), or glycine (G), or serine (S) at position 101 (according to BPN' numbering) and has proteolytic activity. In one embodiment, subtilisin is at least 80%, at least 85%, at least 90%, at least 91%, at least 92%, at least 93%, at least 94%, at least 95%, at least 96%, at least 97%, at least 98% or at least 99% identical or similar to SEQ ID NO:22 as described in EP 1921147 and is characterized by having amino acid glutamic acid (E), or aspartic acid (D), at position 101 (according to BPN' numbering) and has proteolytic activity. In one embodiment, the subtilisin is SEQ ID NO:22 as described in EP 1921147 characterized by an amino acid substitution at position 101, such as R101E or R101D, alone or in combination with one or more substitutions at positions 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and/or 274 (according to BPN' numbering) and has proteolytic activity. In one embodiment, the subtilisin variant comprises an amino acid substitution at position 101, such as R101E or R101D and one or more further substitutions: (a) threonine at position 3 (3T), (b) isoleucine at position 4 (4I), (c) alanine, threonine or arginine at position 63 (63A, 63T, or 63R), (d) aspartic acid or glutamic acid at position 156 (156D or 156E), (e) proline at position 194 (194P), (f) methionine at position 199 (199M), (g) isoleucine at position 205 (205I), (h) aspartic acid, glutamic acid or glycine at position 217 (217D, 217E or 217G), (i) combinations of two or more amino acids according to (a) to (h).

In one embodiment, a lipase variant of the invention has increased stability against proteolytic degradation in the presence of subtilisin 309 or a variant thereof which is at least 80% identical or similar thereto when compared to the lipase according to SEQ ID NO: 1. The subtilisin 309 or a variant thereof may be stabilized or non-stabilized.

In one embodiment, a lipase variant of the invention has increased stability against proteolytic degradation such as non-stabilized subtilisin 309 or a non-stabilized variant thereof which is at least 80% identical or similar thereto, when compared to the lipase according to SEQ ID NO: 1. In another embodiment, a lipase variant of the invention has increased stability against proteolytic degradation in the presence of stabilized subtilisin 309 or in the presence of stabilized variant thereof which is at least 80% identical or similar thereto, when compared to the lipase according to SEQ ID NO: 1.

In one embodiment, a lipase variant of the invention has increased stability against proteolytic degradation when compared to the lipase according to SEQ ID NO: 1, in the presence of at least one subtilisin according to SEQ ID NO: 22 as described in EP 1921147 and variants thereof having proteolytic activity. The variant of SEQ ID NO: 22 as described in EP 1921147 may be a polypeptide sequence which is at least 80% identical or similar SEQ ID NO:22 as described in EP 1921147 and has proteolytic activity. In one embodiment, a subtilisin is at least 80% identical or similar to SEQ ID NO:22 as described in EP 1921147 and is characterized by having amino acid glutamic acid (E), or aspartic acid (D), or asparagine (N), or glutamine (Q), or alanine (A), or glycine (G), or serine (S) at position 101 (according to BPN' numbering) and has proteolytic activity. In one embodiment, subtilisin is at least 80%, at least 85%, at least 90%, at least 91%, at least 92%, at least 93%, at least 94%, at least 95%, at least 96%, at least 97%, at least 98% or at least 99% identical or similar to SEQ ID NO:22 as described in EP 1921147 and is characterized by having amino acid glutamic acid (E), or aspartic acid (D), at position 101 (according to BPN' numbering) and has proteolytic activity. In one embodiment, the subtilisin is SEQ ID NO:22 as described in EP 1921147 characterized by an amino acid substitution at position 101, such as R101E or R101D, alone or in combination with one or more substitutions at positions 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and/or 274 (according to BPN' numbering) and has proteolytic activity. In one embodiment, the subtilisin variant comprises an amino acid substitution at position 101, such as R101E or R101D and one or more further substitutions: (a) threonine at position 3 (3T), (b) isoleucine at position 4 (4I), (c) alanine, threonine or arginine at position 63 (63A, 63T, or 63R), (d) aspartic acid or glutamic acid at position 156 (156D or 156E), (e) proline at position 194 (194P), (f) methionine at position 199 (199M), (g) isoleucine at position 205 (205I), (h) aspartic acid, glutamic acid or glycine at position 217 (217D, 217E or 217G), (i) combinations of two or more amino acids according to (a) to (h). The subtilisin according to SEQ ID NO:22 of EP 1921147 or a variant thereof may be stabilized or non-stabilized.

In another embodiment, a lipase variant of the invention has increased stability against proteolytic degradation such as non-stabilized subtilisin according to SEQ ID NO:22 as described in EP 1921147 or a non-stabilized variant thereof which is at least 80% identical or similar thereto, when compared to the lipase according to SEQ ID NO: 1. In another embodiment, a lipase variant of the invention has increased stability against proteolytic degradation in the presence of stabilized subtilisin according to SEQ ID NO:22 as described in EP 1921147 or a non-stabilized variant thereof which is at least 80% identical or similar thereto, when compared to the lipase according to SEQ ID NO: 1. Variants of said SEQ ID NO: 22 are those as described herein, such as SEQ ID NO: 22 as described in EP 1921147 with the substitution R101E.

In one embodiment, a polypeptide comprising an amino acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence of SEQ ID NO:1 having lipase activity has increased stability against proteolytic degradation when compared to *Thermomyces lanuginosa* lipase according to amino acids 1-269 of SEQ ID NO: 2 of U.S. Pat. No. 5,869,438 and or when compared to *Thermomyces lanuginosa* lipase according to amino acids 1-269 of SEQ ID NO: 2 of U.S. Pat. No. 5,869,438 with amino acid substitutions T231R and N233R, in the presence of at least one subtilisin according to SEQ ID NO: 22 as described in EP 1921147 and variants thereof having proteolytic activity. The variant of SEQ ID NO: 22 as described in EP 1921147 may be a polypeptide sequence which is at least 80% identical or similar SEQ ID NO:22 as described in EP 1921147 and has proteolytic activity. In one embodiment, a subtilisin is at least 80% identical or similar to SEQ ID NO:22 as described in EP 1921147 and is characterized by having amino acid glutamic acid (E), or aspartic acid (D), or asparagine (N), or glutamine (Q), or alanine (A), or glycine (G), or serine (S) at position 101 (according to BPN' numbering) and has proteolytic activity. In one embodiment, subtilisin is at least 80%, at least 85%, at least 90%, at least 91%, at least 92%, at least 93%, at least 94%, at least 95%, at least 96%, at least 97%, at least 98% or at least 99% identical or similar to SEQ ID NO:22 as described in EP 1921147 and is characterized by having amino acid glutamic acid (E), or aspartic acid (D), at position 101 (according to BPN' numbering) and has proteolytic activity. In one embodiment, the subtilisin is SEQ ID NO:22 as described in EP 1921147 characterized by an amino acid substitution at position 101, such as R101E or R101D, alone or in combination with one or more substitutions at positions 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and/or 274 (according to BPN' numbering) and has proteolytic activity. In one embodiment, the subtilisin variant comprises an amino acid substitution at position 101, such as R101E or R101D and one or more further substitutions: (a) threonine at position 3 (3T), (b) isoleucine at position 4 (4I), (c) alanine, threonine or arginine at position 63 (63A, 63T, or 63R), (d) aspartic acid or glutamic acid at position 156 (156D or 156E), (e) proline at position 194 (194P), (f) methionine at position 199 (199M), (g) isoleucine at position 205 (205I), (h) aspartic acid, glutamic acid or glycine at position 217 (217D, 217E or 217G), (i) combinations of two or more amino acids according to (a) to (h). The subtilisin according to SEQ ID NO:22 of EP 1921147 or a variant thereof may be stabilized or non-stabilized.

In one embodiment, a polypeptide according to amino acid sequence of SEQ ID NO:1 has increased stability against proteolytic degradation when compared to *Thermomyces lanuginosa* lipase according to amino acids 1-269 of SEQ ID NO: 2 of U.S. Pat. No. 5,869,438 and or when compared to *Thermomyces lanuginosa* lipase according to amino acids 1-269 of SEQ ID NO: 2 of U.S. Pat. No. 5,869,438 with amino acid substitutions T231R and N233R, in the presence of subtilisin 309 or a variant thereof which is at least 80% identical or similar thereto, wherein the subtilisin may be stabilized or non-stabilized.

In one embodiment, a lipase variant of SEQ ID NO:1 as disclosed herein has increased stability against proteolytic degradation when compared to *Thermomyces lanuginosa* lipase according to amino acids 1-269 of SEQ ID NO: 2 of U.S. Pat. No. 5,869,438 and or when compared to *Thermomyces lanuginosa* lipase according to amino acids 1-269 of SEQ ID NO: 2 of U.S. Pat. No. 5,869,438 with amino acid substitutions T231R and N233R, in the presence of subtilisin 309 or a variant thereof which is at least 80% identical or similar thereto. The subtilisin 309 or a variant thereof may be stabilized or non-stabilized.

In one embodiment, a polypeptide according to amino acid sequence of SEQ ID NO:1 has increased stability against proteolytic degradation when compared to *Thermomyces lanuginosa* lipase according to amino acids 1-269 of SEQ ID NO: 2 of U.S. Pat. No. 5,869,438 and or when compared to *Thermomyces lanuginosa* lipase according to amino acids 1-269 of SEQ ID NO: 2 of U.S. Pat. No. 5,869,438 with amino acid substitutions T231R and N233R, in the presence of a subtilisin according to SEQ ID NO: 22 as described in EP 1921147 with amino acid substitution R101E, wherein the subtilisin may be stabilized or non-stabilized.

In one embodiment, a lipase variant of SEQ ID NO:1 as disclosed herein has increased stability against proteolytic degradation when compared to *Thermomyces lanuginosa* lipase according to amino acids 1-269 of SEQ ID NO: 2 of U.S. Pat. No. 5,869,438 and or when compared to *Thermomyces lanuginosa* lipase according to amino acids 1-269 of SEQ ID NO: 2 of U.S. Pat. No. 5,869,438 with amino acid substitutions T231R and N233R, in the presence of a subtilisin according to SEQ ID NO: 22 as described in EP 1921147 with amino acid substitution R101E, wherein the subtilisin may be stabilized or non-stabilized.

Protease stabilizers may be selected from boron-containing compounds. Boron-containing compounds are selected from boric acid or its derivatives and from boronic acid or its derivatives such as aryl boronic acids or its derivatives, from salts thereof, and from mixtures thereof. Boric acid herein may be called orthoboric acid.

In one embodiment, boron-containing compound is selected from the group consisting of aryl boronic acids and its derivatives. In one embodiment, boron-containing compound is selected from the group consisting of benzene boronic acid (BBA) which is also called phenyl boronic acid (PBA), derivatives thereof, and mixtures thereof. In one embodiment, phenyl boronic acid derivatives are selected from the group consisting of the derivatives of formula (I) and (II) formula:

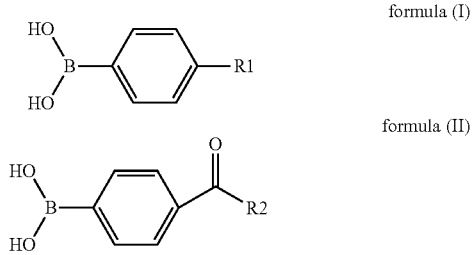

Wherein R1 is selected from the group consisting of hydrogen, hydroxy, non-substituted or substituted $C_1$-$C_6$ alkyl, and non-substituted or substituted $C_1$-$C_6$ alkenyl; in a preferred embodiment, R is selected from the group consisting of hydroxy, and non-substituted $C_1$ alkyl.

Wherein R2 is selected from the group consisting of hydrogen, hydroxy, non-substituted or substituted $C_1$-$C_6$ alkyl, and non-substituted or substituted $C_1$-$C_6$ alkenyl; in a preferred embodiment, R is selected from the group consisting of H, hydroxy, and substituted $C_1$ alkyl.

In one embodiment phenyl-boronic acid derivatives are selected from the group consisting of 4-formyl phenyl boronic acid (4-FPBA), 4-carboxy phenyl boronic acid (4-CPBA), 4-(hydroxymethyl) phenyl boronic acid (4-HMPBA), and p-tolylboronic acid (p-TBA).

Other suitable derivatives include: 2-thienyl boronic acid, 3-thienyl boronic acid, (2-acetamido-phenyl) boronic acid, 2-benzofuranyl boronic acid, 1-naphthyl boronic acid, 2-naphthyl boronic acid, 2-FPBA, 3-FBPA, 1-thianthrenyl boronic acid, 4-dibenzofuran boronic acid, 5-methyl-2-thienyl boronic acid, 1-benzothiophene-2 boronic acid, 2-furanyl boronic acid, 3-furanyl boronic acid, 4,4 biphenyl-diboronic acid, 6-hydroxy-2-naphthaleneboronic acid, 4-(methylthio) phenyl boronic acid, 4-(trimethylsilyl) phenyl boronic acid, 3-bromothiophene boronic acid, 4-methylthiophene boronic acid, 2-naphthyl boronic acid, 5-bromothiophene boronic acid, 5-chlorothiophene boronic acid, dimethylthiophene boronic acid, 2-bromophenyl boronic acid, 3-chlorophenyl boronic acid, 3-methoxy-2-thiophene boronic acid, p-methyl-phenylethyl boronic acid, 2-thianthrenyl boronic acid, di-benzothiophene boronic acid, 9-anthracene boronic acid, 3,5 dichlorophenyl boronic, acid, diphenyl boronic acid anhydride, o-chlorophenyl boronic acid, p-chlorophenyl boronic acid, m-bromophenyl boronic acid, p-bromophenyl boronic acid, p-fluoro-phenyl boronic acid, octyl boronic acid, 1,3,5 trimethylphenyl boronic acid, 3-chloro-4-fluoro-phenyl boronic acid, 3-aminophenyl boronic acid, 3,5-bis-(trifluoromethyl) phenyl boronic acid, 2,4 dichlorophenyl boronic acid, 4-methoxyphenyl boronic acid, and mixtures thereof.

In one embodiment, at least one boron-containing compound is used together with at least one polyol containing from 2 to 6 hydroxyl groups to stabilize protease. Suitable examples include glycol, propylene glycol, 1,2-propane diol, 1,2-butane diol, ethylene glycol, hexylene glycol, glycerol, sorbitol, mannitol, erythriol, glucose, fructose, lactore, and erythritan.

The variant polypeptides of the invention may be used in several industries where lipases are useful in processing applications and/or where lipases are useful components of formulations.

In one aspect, the invention is related to the use of the variant polypeptides of the invention in processing of fats, oils or oilseed in food and/or feed processes preferably during cleaning or washing textiles, hard surfaces, or dishes; during processing pulp or paper; and/or during ethanol production:

The lipase variants of the invention may be used in food formulations, for example the enzyme can be an additive for baking (see WO 2017/142904). In one embodiment, the inventive polypeptides having lipase activity can be used in a method of preparing a dough, or in a baked product prepared from the dough, wherein the method comprises the steps of (a) adding the polypeptides having lipase activity to the dough and (b) baking it.

The lipase variants of the invention may be used in the oilseed processing industry, for example the enzyme is use for processing plant (soy, canola) oil (WO 2005/086900). In one embodiment, the inventive polypeptides having lipase activity can be used in a method for processing fats, oils, or oilseeds; wherein the method comprises (a) providing a fat, an oil, or an oilseed; (b) providing a polypeptide having lipase activity; and (c) contacting the polypeptide with the fat, the oil, or the oilseed, wherein the polypeptide hydrolyses the fat to a desired product.

The lipase variants of the invention may be used in feed formulations (see U.S. Pat. No. 8,735,123). In one embodiment, the inventive polypeptides having lipase activity can be used in a method for feeding an animal; wherein the method comprises (a) providing a feed formulation or pellet, (b) providing the lipase in the feed formulation or pellet, and (c) feeding the animal the feed formulation.

The lipase variants of the invention may be used in the starch processing industry, for example to process byproducts such as oil in the process of conversion of starch to ethanol or sugars with amylases (high fructose corn syrup) (see WO 2004/029193). In one embodiment, the inventive polypeptides having lipase activity can be used in a method for making ethanol, wherein in the method comprises, (a) providing a material from ethanol production, wherein the material has an oil, (b) providing a lipase, and (c) contacting the material with the lipase, wherein the lipase helps improving the recovery of oil from the material. In another embodiment, the lipase variants of the invention can be used in biodiesel production (U.S. Pat. No. 7,550,278).

The lipase variants of the invention may be used in in pulp and paper processing, for example, the enzymes (lipase) can be used for improving paper strength (see WO 2006/031699), and pitch control (see U.S. 2010/0269989). In one embodiment, the inventive polypeptides having lipase activity can be used in a method for processing pulp or paper, wherein the method comprises (a) providing a pulp or paper, (b) providing a lipase, and (c) contacting the pulp or paper with the lipase, wherein the lipase improves the strength of the pulp or paper.

The lipase variants of the invention may be used for mining and oil well services, for example cellulases, amylases, and/or lipases can be used for breaking guar during oil well fracturing (U.S. Pat. No. 5,725,771).

The lipase variants of the invention may be used in detergent formulations or cleaning formulations. In one embodiment, the inventive polypeptides having lipase activity can be used in a method of cleaning or washing textiles, hard surfaces, or dishes, wherein the method comprises, (a) providing a textiles, hard surfaces, or dishes, (b) providing a lipase, and (c) contacting the textiles, hard surfaces, or dishes, and the lipase, wherein the lipase removes a fatty stain from the textiles, hard surfaces, or dishes.

The invention relates to detergent formulations or cleaning formulations comprising at least one lipase variant of the invention and at least one detergent component. "Detergent formulation" or "cleaning formulation" means compositions designated for cleaning soiled material. Cleaning includes laundering and hard surface cleaning. Soiled material according to the invention includes textiles and/or hard surfaces.

The term "laundering" relates to both household laundering and industrial laundering and means the process of treating textiles with a solution containing a detergent composition of the present invention. The laundering process may be carried out by using technical devices such as a household or an industrial washing machine. Alternatively, the laundering process may be done by hand.

The term "textile" means any textile material including yarns (thread made of natural or synthetic fibers used for knitting or weaving), yarn intermediates, fibers, non-woven materials, natural materials, synthetic materials, as well as fabrics (a textile made by weaving, knitting or felting fibers) made of these materials such as garments (any article of clothing made of textile), cloths and other articles.

The term "fibers" includes natural fibers, synthetic fibers, and mixtures thereof. Examples of natural fibers are of plant (such as flax, jute and cotton) or animal origin, comprising proteins like collagen, keratin and fibroin (e.g. silk, sheep wool, angora, mohair, cashmere). Examples for fibers of synthetic origin are polyurethane fibers such as Spandex® or Lycra®, polyester fibers, polyolefins such as elastofin, or polyamide fibers such as nylon. Fibers may be single fibers or parts of textiles such as knitwear, wovens, or nonwovens.

The term "hard surface cleaning" is defined herein as cleaning of hard surfaces wherein hard surfaces may include any hard surfaces in the household, such as floors, furnishing, walls, sanitary ceramics, glass, metallic surfaces including cutlery or dishes.

The term "dish wash" refers to all forms of washing dishes, e.g. by hand or automatic dish wash. Dish washing includes, but is not limited to, the cleaning of all forms of crockery such as plates, cups, glasses, bowls, all forms of cutlery such as spoons, knives, forks and serving utensils as well as ceramics, plastics such as melamine, metals, china, glass and acrylics.

The detergent formulation of the invention comprises one or more detergent component(s). The component(s) chosen depend on the desired cleaning application and/or physical form of a detergent composition.

The term "detergent component" is defined herein to mean any types of ingredient, which is suitable for detergent compositions, such as surfactants, building agents, polymers, bleaching systems. Any component(s) known in the art acknowledging their known characteristics are suitable detergent component(s) according to the invention. Detergent components in one embodiment means components which provide washing or cleaning performance or which effectively aid the processing (maintain physical characteristics during processing, storage and use; e.g. rheology modifiers, hydrotropes, desiccants) when present in effective amounts.

Usually, a detergent composition is a complex formulation of more than two detergent components.

Detergent components may have more than one function in the final application of a detergent formulation, therefore any detergent component mentioned in the context of a specific function herein, may also have another function in the final application of a detergent formulation. The function of a specific detergent component in the final application of a detergent formulation usually depends on its amount within the detergent formulation, i.e. the effective amount of a detergent component.

The term "effective amount" includes amounts of individual components to provide effective stain removal and effective cleaning conditions (e.g. pH, quantity of foaming), amounts of certain components to effectively provide optical benefits (e.g. optical brightening, dye transfer inhibition), and amounts of certain components to effectively aid the processing (maintain physical characteristics during processing, storage and use; e.g. rheology modifiers, hydrotropes, desiccants).

In one embodiment, a detergent formulation is a formulation of more than two detergent components, wherein at least one component is effective in stain-removal, at least one component is effective in providing the optimal cleaning conditions, and at least one component is effective in maintaining the physical characteristics of the detergent.

Cleaning performance is evaluated under relevant cleaning conditions. The term "relevant cleaning conditions" herein refers to the conditions, particularly cleaning temperature, time, cleaning mechanics, suds concentration, type of detergent and water hardness, actually used in laundry machines, automatic dish washers or in manual cleaning processes.

Cleaning performance of lipase containing detergents may be called degreasing performance herein. Degreasing performance may be related to the ability of the detergent formulation to remove fatty stains deposited on textiles.

Fats can be sub-classified as fat, grease or oil depending on the melting temperature. Oil is usually liquid at room temperature. Grease has a higher viscosity than oil at room temperature and be called pasty. The removal of oily and greasy stains deposited on textiles, due to the relatively low melting temperature of oil and grease, is supported by laundering temperatures >40° C. Fatty deposits comprising fatty compounds having a melting temperature >30° C., means fats remaining solid at temperatures ≤30° C.

Fatty stains deposited on textiles may be called fatty deposits herein. In one embodiment, fatty deposits comprise fatty compounds having a melting point >40° C., meaning that such fatty compounds remain solid at laundering temperatures ≤40° C. In one embodiment, fatty deposits comprise fatty compounds having a melting point >30° C., meaning that such fatty compounds remain solid at laundering temperatures ≤30° C.

In one aspect, the invention relates to a solid or liquid laundry formulation for laundering temperatures ≤40° C. comprising at least one lipase variant of the invention and the use of said formulation to remove fatty deposits comprising fatty compounds having a melting temperature >40° C. at laundering temperatures ≤40° C. In one embodiment, the invention relates to a solid or liquid laundry formulation for laundering temperatures ≤30° C. comprising at least one lipase variant of the invention and the use of said formulation to remove fatty deposits comprising fatty compounds having a melting temperature >40° C. at laundering temperatures ≤30° C. In one embodiment, the invention relates to a solid or liquid laundry formulation for laundering temperatures ≤30° C. comprising at least one lipase variant of the invention and the use of said formulation to remove fatty deposits comprising fatty compounds having a melting temperature >30° C. at laundering temperatures ≤30° C. In one embodiment, the invention relates to a solid or liquid laundry formulation for laundering temperatures ≤25° C. comprising at least one lipase variant of the invention and the use of said formulation to remove fatty deposits comprising fatty compounds having a melting temperature >25° C. at laundering temperatures ≤25° C. In one embodiment, the invention relates to a solid or liquid laundry formulation for laundering temperatures ≤25° C. comprising at least one lipase variant of the invention and the use of said formulation to remove fatty deposits comprising fatty compounds having a melting temperature >30° C. at laundering temperatures ≤25° C.

Degreasing performance herein is meant to be improved when removal of fatty stains is improved. Improved in this context may mean that the inventive lipase and/or detergent formulation comprising at least one inventive lipase shows better degreasing performance when compared to non-inventive lipase and/or laundry formulations lacking inventive lipases and/or laundry formulations comprising the parent lipase. The removal of fatty stains may occur due to enzymatic degradation and/or solubilization and/or dispersion and/or emulsifying of the fatty compounds deposited on textile.

In one aspect, the invention relates to a solid or liquid laundry formulation comprising
(a) at least one lipase, wherein at least one lipase is selected from a polypeptide comprising an amino acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence of SEQ ID NO:1,
(b) at least one protease, wherein at least one protease is selected from subtilisin comprising a polypeptide sequence which is at least 80%, at least 85%, at least 90%, at least 91%, at least 92%, at least 93%, at least 94%, at least 95%, at least 96%, at least 97%, at least 98% or at least 99% identical or similar to SEQ ID NO:22 as described in EP 1921147 and is characterized by having amino acid substitution at position 101 (according to BPN' numbering) and has proteolytic activity, and
(c) at least one detergent component in effective amounts.

In one embodiment, the subtilisin is SEQ ID NO:22 as described in EP 1921147 characterized by an amino acid substitution at position 101, such as R101E or R101D, alone or in combination with one or more one or more further substitutions: (a) threonine at position 3 (3T), (b) isoleucine at position 4 (4I), (c) alanine, threonine or arginine at position 63 (63A, 63T, or 63R), (d) aspartic acid or glutamic acid at position 156 (156D or 156E), (e) proline at position 194 (194P), (f) methionine at position 199 (199M), (g) isoleucine at position 205 (205I), (h) aspartic acid, glutamic acid or glycine at position 217 (217D, 217E or 217G), (i) combinations of two or more amino acids according to (a) to (h). In one embodiment subtilisin is SEQ ID NO:22 as described in EP 1921147 with amino acid substitution R101E.

In one embodiment, the solid or liquid laundry formulation comprises
(a) at least one lipase comprising an amino acid sequence that is at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical or similar to the full length amino acid sequence of SEQ ID NO:1,
(b) a subtilisin according to SEQ ID NO:22 as described in EP 1921147 with amino acid substitution R101E, and
(c) at least one detergent component in effective amounts.

In one embodiment, the solid or liquid laundry formulation comprises
(a) a lipase according to amino acid sequence of SEQ ID NO:1,
(b) a subtilisin according to SEQ ID NO:22 as described in EP 1921147 with amino acid substitution R101E, and
(c) at least one detergent component in effective amounts.

In one embodiment, the subtilisin is SEQ ID NO:22 as described in EP 1921147 characterized by an amino acid substitution at position 101, such as R101E or R101D, alone or in combination with one or more one or more further substitutions: (a) threonine at position 3 (3T), (b) isoleucine at position 4 (4I), (c) alanine, threonine or arginine at position 63 (63A, 63T, or 63R), (d) aspartic acid or glutamic acid at position 156 (156D or 156E), (e) proline at position 194 (194P), (f) methionine at position 199 (199M), (g) isoleucine at position 205 (205I), (h) aspartic acid, glutamic acid or glycine at position 217 (217D, 217E or 217G), (i) combinations of two or more amino acids according to (a) to (h). In one embodiment subtilisin is SEQ ID NO:22 as described in EP 1921147 with amino acid substitution R101E.

In one embodiment, the laundry formulation comprising (a) a lipase, (b) a subtilisin, and (c) at least one detergent component as disclosed above, is used for removing fatty deposits comprising fatty compounds having a melting temperature >40° C. at laundering temperatures selected from ≤40° C., ≤30° C., and ≤25° C. In one embodiment, the laundry formulation comprising (a) a lipase, (b) a subtilisin, and (c) at least one detergent component as disclosed above is used for removing fatty deposits comprising fatty compounds having a melting temperature >30° C. at laundering temperatures selected from ≤30° C., and ≤25° C. In one embodiment, the laundry formulation comprising (a) a lipase, (b) a subtilisin, and (c) at least one detergent component as disclosed above is used for removing fatty deposits comprising fatty compounds having a melting temperature >25° C. at laundering temperatures ≤25° C.

Individual detergent components and usage in detergent compositions are known to those skilled in the art. Suitable detergent components comprise inter alia surfactants, builders, polymers, alkaline, bleaching systems, fluorescent whitening agents, suds suppressors and stabilizers, hydrotropes, and corrosion inhibitors. Further examples are described e.g. in "complete Technology Book on Detergents with Formulations (Detergent Cake, Dishwashing Detergents, Liquid & Paste Detergents, Enzyme Detergents, Cleaning Powder & Spray Dried Washing Powder)", Engineers India Research Institute (EIRI), 6th edition (2015). Another reference book for those skilled in the art may be "Detergent Formulations Encyclopedia", Solverchem Publications, 2016.

Detergent components vary in type and/or amount in a detergent formulation depending on the desired application such as laundering white textiles, colored textiles, and wool. The component(s) chosen further depend on physical form of a detergent formulation (liquid, solid, gel, provided in pouches or as a tablet, etc). The component(s) chosen e.g. for laundering formulations further depend on regional conventions which themselves are related to aspects like washing temperatures used, mechanics of laundry machine (vertical vs. horizontal axis machines), water consumption per wash cycle etc. and geographical characteristics like average hardness of water.

For example: A low detergent concentration system includes laundering formulations where less than about 800 ppm of detergent components are present in the wash water. A medium detergent concentration includes laundering formulations where between about 800 ppm and about 2,000 ppm of detergent components are present in the wash water. A high detergent concentration includes laundering formulations where more than about 2,000 ppm of detergent components are present in the wash water.

The numeric ranges recited for the individual detergent components provide amounts comprised in detergent compositions. Such ranges have to be understood to be inclusive of the numbers defining the range and include each integer within the defined range.

If not described otherwise, "% by weight" or "% w/w" is meant to be related to total detergent composition. In this case "% by weight" or "% w/w" is calculated as follows: concentration of a substance as the weight of that substance divided by the total weight of the composition, multiplied by 100.

Detergent formulations of the invention may comprise one or more surfactant(s). "Surfactant" (synonymously used herein with "surface active agent") means an organic chemical that, when added to a liquid, changes the properties of that liquid at an interface. According to its ionic charge, a surfactant is called non-ionic, anionic, cationic, or amphoteric.

Non-limiting examples of surfactants are disclosed McCutcheon's 2016 Detergents and Emulsifiers, and McCutcheon's 2016 Functional Materials, both North American and International Edition, MC Publishing Co, 2016 edition. Further useful examples are disclosed in earlier editions of the same publications which are known to those skilled in the art.

Non-ionic surfactant means a surfactant that contains neither positively nor negatively charged (i.e. ionic) functional groups. In contrast to anionic and cationic surfactants, non-ionic surfactants do not ionize in solution.

Examples provided below for surfactants of any kind are to be understood to be non-limiting.

In one embodiment, the detergent formulation of the invention comprises at least one non-ionic surfactant. Non-ionic surfactants may be compounds of the general formula (III):

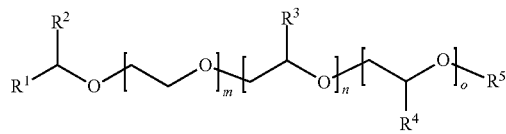

(III)

The variables of the general formula (III) are defined as follows:

$R^1$ is selected from $C_1$-$C_{23}$ alkyl and $C_2$-$C_{23}$ alkenyl, wherein alkyl and/or alkenyl are linear or branched; examples are n-$C_7H_{15}$, n-$C_9H_{19}$, n-$C_{11}H_{23}$, n-$C_{13}H_{27}$, n-$C_{15}H_{31}$, n-$C_{17}H_{35}$, i-$C_9H_{19}$, i-$C_{12}H_{25}$.

$R^2$ is selected from H, $C_1$-$C_{20}$ alkyl and $C_2$-$C_{20}$ alkenyl, wherein alkyl and/or alkenyl are linear or branched.

$R^3$ and $R^4$, each independently selected from $C_1$-$C_{16}$ alkyl, wherein alkyl is linear or branched; examples are methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, isodecyl.

$R^5$ is selected from H and $C_1$-$C_{18}$ alkyl, wherein alkyl is linear or branched.

The integers of the general formula (III) are defined as follows: m is in the range of zero to 200, preferably 1-80, more preferably 3-20; n and o, each independently in the range of zero to 100; n preferably is in the range of 1 to 10, more preferably 1 to 6; o preferably is in the range of 1 to 50, more preferably 4 to 25. The sum of m, n and o is at least one, preferably the sum of m, n and o is in the range of 5 to 100, more preferably in the range of from 9 to 50.

The non-ionic surfactants of the general formula (III) may be of any structure, is it block or random structure, and is not limited to the displayed sequences.

In one embodiment, the detergent formulation comprises at least one non-ionic surfactant selected from general formula (III), wherein m is in the range of 3 to 11, preferably not more than 7; n and o is 0, $R^1$ is $C_{12}$-$C_{14}$, $R^5$ is H. The detergent formulation may comprise at least two non-ionic surfactants, selected from compounds of general formula (III), wherein one of said non-ionic surfactants is characterized in $R^1$ being $C_{12}$, $R^5$ being H, m is 7, n and o=0, and the other surfactant is characterized in $R^1$ being $C_{14}$, $R^5$ being H, m being 7, n and o=0.

Non-ionic surfactants may further be compounds of the general formula (IV), which might be called alkyl-polyglycosides (APG):

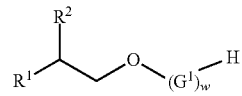

(IV)

The variables of the general formula (IV) are defined as follows:

$R^1$ is selected from $C_1$-$C_{17}$ alkyl and $C_2$-$C_{17}$ alkenyl, wherein alkyl and/or alkenyl are linear or branched; examples are n-$C_7H_{15}$, n-$C_9H_{19}$, n-$C_{11}H_{23}$, n-$C_{13}H_{27}$, n-$C_{15}H_{31}$, n-$C_{17}H_{35}$, i-$C_9H_{19}$, i-$C_{12}H_{25}$.

$R^2$ is selected from H, $C_1$-$C_{17}$ alkyl and $C_2$-$C_{17}$ alkenyl, wherein alkyl and/or alkenyl are linear or branched.

$G^1$ is selected from monosaccharide residues with 4 to 6 carbon atoms, such as glucose and xylose.

The integer w of the general formula (IV) is in the range of from 1.1 to 4, w being an average number.

Non-ionic surfactants may further be compounds of general formula (V):

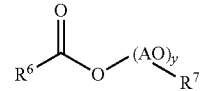

(V)

The variables of the general formula (V) are defined as follows:

AO is selected from ethylene oxide (EO), propylene oxide (PO), butylene oxide (BO), and mixtures thereof.

$R^6$ is selected from $C_5$-$C_{17}$ alkyl and $C_5$-$C_{17}$ alkenyl, wherein alkyl and/or alkenyl are linear or branched $R^7$ is selected from H, $C_1$-$C_{18}$-alkyl, wherein alkyl is linear or branched.

The integer y of the general formula (V) is a number in the range of 1 to 70, preferably 7 to 15.

Non-ionic surfactants may further be selected from sorbitan esters and/or ethoxylated or propoxylated sorbitan esters. Non-limiting examples are products sold under the trade names SPAN and TWEEN.

Non-ionic surfactants may further be selected from alkoxylated mono- or di-alkylamines, fatty acid monoethanolamides (FAMA), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), and combinations thereof.

Mixtures of two or more different non-ionic surfactants may also be present in detergent formulations according to the present invention.

In one embodiment, the detergent formulation of the invention comprises at least one surfactant selected from amphoteric surfactants. Amphoteric surfactants are those, depending on pH, which can be either cationic, zwitterionic or anionic; amphoteric surfactants are known to those skilled in the art. Generally: Amphoteric surfactants may be compounds which are called modified amino acids (proteinogenic as well as non-proteinogenic). Amphoteric surfactants may further be compounds called betaines and/or sulfobetaines, alkyl-amphocarboxylates, and amine oxides (AO).

Mixtures of two or more different amphoteric surfactants may be present in detergent compositions according to the present invention.

Anionic surfactant means a surfactant with a negatively charged ionic group. Anionic surfactants include, but are not limited to, surface-active compounds that contain a hydrophobic group and at least one water-solubilizing anionic group, usually selected from sulfates, sulfonate, and carboxylates to form a water-soluble compound.

Anionic surfactants may be compounds of general formula (VI), which might be called (fatty) alcohol/alkyl (ethoxy/ether) sulfates [(F)A(E)S] when $A^-$ is $SO_3^-$, (fatty) alcohol/alkyl (ethoxy/ether) carboxylat [(F)A(E)C] when $A^-$ is $-RCOO^-$:

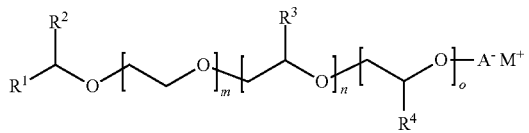

(VI)

The variables in general formula (VI) are defined as follows:
$R^1$ is selected from $C_1$-$C_{23}$-alkyl (such as 1-, 2-, 3-, 4-$C_1$-$C_{23}$-alkyl) and $C_2$-$C_{23}$-alkenyl, wherein alkyl and/or alkenyl are linear or branched, and wherein 2-, 3-, or 4-alkyl; examples are n-$C_7H_{15}$, n-$C_9H_{19}$, n-$C_{11}H_{23}$, n-$C_{13}H_{27}$, n-$C_{15}H_{31}$, n-$C_{17}H_{35}$, i-$C_9H_{19}$, i-$C_{12}H_{25}$.
$R^2$ is selected from H, $C_1$-$C_{20}$-alkyl and $C_2$-$C_{20}$-alkenyl, wherein alkyl and/or alkenyl are linear or branched.
$R^3$ and $R^4$, each independently selected from $C_1$-$C_{16}$-alkyl, wherein alkyl is linear or branched; examples are methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, isodecyl.
$A^-$ is selected from $-RCOO^-$, $-SO_3^-$ and $RSO_3^-$, wherein R is selected from linear or branched $C_1$-$C_8$-alkyl, and $C_1$-$C_4$ hydroxyalkyl, wherein alkyl is.

$M^+$ is selected from H and salt forming cations. Salt forming cations may be monovalent or multivalent; hence $M^+$ equals $1/v\ M^{v+}$. Examples include but are not limited to sodium, potassium, magnesium, calcium, ammonium, and the ammonium salt of mono-, di, and triethanolamine.

The integers of the general formulae (VI) are defined as follows: m is in the range of zero to 200, preferably 1-80, more preferably 3-20; n and o, each independently in the range of zero to 100; n preferably is in the range of 1 to 10, more preferably 1 to 6; o preferably is in the range of 1 to 50, more preferably 4 to 25. The sum of m, n and o is at least one, preferably the sum of m, n and o is in the range of 5 to 100, more preferably in the range of from 9 to 50.

Anionic surfactants of the general formula (VI) may be of any structure, block copolymers or random copolymers.

Further suitable anionic surfactants include salts ($M^+$) of $C_{12}$-$C_{18}$ sulfo fatty acid alkyl esters (such as $C_{12}$-$C_{18}$ sulfo fatty acid methyl esters), $C_{10}$-$C_{18}$-alkylarylsulfonic acids (such as n-$C_{10}$-$C_{18}$-alkylbenzene sulfonic acids) and $C_{10}$-$C_{18}$ alkyl alkoxy carboxylates.

$M^+$ in all cases is selected from salt forming cations. Salt forming cations may be monovalent or multivalent; hence $M^+$ equals $1/v\ M^{v+}$. Examples include but are not limited to sodium, potassium, magnesium, calcium, ammonium, and the ammonium salt of mono-, di, and triethanolamine.

In one embodiment, the detergent formulation comprises at least one anionic surfactant selected from compounds of general formula (VI), wherein $R^1$ is $C_{11}$-$C_{13}$, R2 is H, m is 1-4, n and o=0, $A^-$ is $SO_3$, $M^+$ is $Na^+$. The detergent formulation may comprise at least two anionic surfactants, selected from compounds of general formula (VI), wherein one of said anionic surfactants is characterized in $R^1$ being $C_{11}$, $R^2$ being H, m being 2, n and o=0, $A^-$ being $SO_3^-$, $M^+$ being $Na^+$ and the other surfactant is characterized in $R^1$ being $C_{13}$, $R^2$ being H, m being 2, n and o=0, $A^-$ being $SO_3^-$, $M^+$ being $Na^+$.

Non-limiting examples of further suitable anionic surfactants include branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, secondary alkanesulfonates (SAS), paraffin sulfonates (PS), sulfonated fatty acid glycerol esters, alkyl- or alkenylsuccinic acid, fatty acid derivatives of amino acids, diesters and monoesters of sulfo-succinic acid.

In one embodiment, the detergent formulation comprises at least one anionic surfactant selected from compounds of general formula (VII):

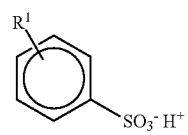

(VII)

wherein $R^1$ in formula (VII) is $C_{10}$-$C_{13}$ alkyl. The detergent formulation may comprise at least two anionic surfactants, selected from compounds of general formula (VII), wherein one of said anionic surfactants is characterized in $R^1$ being $C_{10}$, and the other surfactant is characterized in $R^1$ being $C_{13}$.

Anionic surfactants may be compounds of general formula (VIII), which might be called N-acyl amino acid surfactants:

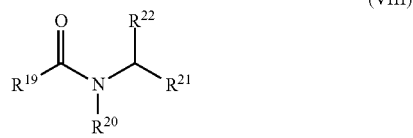

(VIII)

The variables in general formula (VIII) are defined as follows:

$R^{19}$ is selected from linear or branched $C_6$-$C_{22}$-alkyl and linear or branched $C_6$-$C_{22}$-alkenyl such as oleyl.

$R^{20}$ is selected from H and $C_1$-$C_4$-alkyl.

$R^{21}$ is selected from H, methyl, —$(CH_2)_3NHC(NH)NH_2$, —$CH_2C(O)NH_2$, —$CH_2C(O)OH$, —$(CH_2)_2C(O)NH_2$, —$(CH_2)_2C(O)OH$, (imidazole-4-yl)-methyl, —$CH(CH_3)$ $C_2H_5$, —$CH_2CH(CH_3)_2$, —$(CH_2)_4NH_2$, benzyl, hydroxymethyl, —$CH(OH)CH_3$, (indole-3-yl)-methyl, (4-hydroxy-phenyl)-methyl, isopropyl, —$(CH_2)_2SCH_3$, and —$CH_2SH$.

$R^{22}$ is selected from —COOX and —$CH_2SO_3X$, wherein X is selected from $Li^+$, $Na^+$ and $K^+$.

Non-limiting examples of suitable N-acyl amino acid surfactants are the mono- and di-carboxylate salts (e.g., sodium, potassium, ammonium and ammonium salt of mono-, di, and triethanolamine) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and ammonium salt of mono-, di, and triethanolamine) of N-acylated alanine, for example, sodium cocoyl alaninate, and triethanolamine lauroyl alaninate; the carboxylate salts (e.g., sodium, potassium, ammonium and ammonium salt of mono-, di, and triethanolamine) of N-acylated glycine, for example, sodium cocoyl glycinate, and potassium cocoyl glycinate; the carboxylate salts (e.g., sodium, potassium, ammonium and ammonium salt of mono-, di, and triethanolamine) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate.

Anionic surfactants may further be selected from the group of soaps. Suitable are salts ($M^+$) of saturated and unsaturated $C_{12}$-$C_{18}$ fatty acids, such as lauric acid, myristic acid, palmitic acid, stearic acid, behenic acid, oleic acid, (hydrated) erucic acid. $M^+$ is selected from salt forming cations. Salt forming cations may be monovalent or multivalent; hence $M^+$ equals $1/v\ M^{v+}$. Examples include but are not limited to sodium, potassium, magnesium, calcium, ammonium, and the ammonium salt of mono-, di, and triethanolamine.

Further non-limiting examples of suitable soaps include: soap mixtures derived from natural fatty acids such as tallow, coconut oil, palm kernel oil, laurel oil, olive oil, or canola oil. Such soap mixtures comprise soaps of lauric acid and/or myristic acid and/or palmitic acid and/or stearic acid and/or oleic acid and/or linoleic acid in different amounts, depending on the natural fatty acids from which the soaps are derived.

Further non-limiting examples of suitable anionic surfactants include: salts ($M^+$) of sulfates, sulfonates or carboxylates derived from natural fatty acids such as tallow, coconut oil, palm kernel oil, laurel oil, olive oil, or canola oil. Such anionic surfactants comprise sulfates, sulfonates or carboxylates of lauric acid and/or myristic acid and/or palmitic acid and/or stearic acid and/or oleic acid and/or linoleic acid in different amounts, depending on the natural fatty acids from which the soaps are derived.

Mixtures of two or more different anionic surfactants may also be present in detergent compositions according to the present invention.

Mixtures of non-ionic and/or amphoteric and/or anionic surfactants may also be present in detergent compositions according to the present invention.

In one embodiment, the detergent formulation of the invention comprises at least one cationic surfactant meaning a surfactant with a positively charged ionic group. Typically, these cationic moieties are nitrogen containing groups such as quaternary ammonium or protonated amino groups. The cationic protonated amines can be primary, secondary, or tertiary amines.

The detergent formulation may comprise a mixture of surfactants selected from compounds of general formula (III), compounds of general formula (VI), and compounds of general formula (VII).

EXAMPLES

Example 1: ELISA Assay

Enzyme linked immunosorbent assay (ELISA) was used to determine the quantity of lipase expressed and secreted. Polyclonal antibodies were generated to SEQ ID NO:1 and purified by standard methods (primary antibody). A competitive ELISA was employed by coating the plates with purified lipase (SEQ ID NO: 1) then blocking to minimize non-specific binding. Each sample was mixed with primary antibody before incubating on the plate to compete with the pre-coated enzyme. The plates were washed before incubation with a purchased secondary antibody. The plates were washed then commercial development solution was used and the final data read at 450 nm.

Example 2: pNPC8 Assay

Lipase activity was measured by following release of p-nitrophenol from hydrolysis of 4-nitrophenyl octanoate (pNP-C8). By linking a fatty acid to the p-nitrophenol it is possible to follow lipolytic activity by detecting the liberation of p-nitrophenol at 405 nm. Lipases were expressed and the secreted lipase separated from the cells by centrifugation. The supernatants were added to the assay buffer (pNP-C8, Hepes pH 7.5, Sorbitol, Triton X100, and BPER) in 96-well plate format. The absorbance at 405 nm was detected every 30 seconds for 2 to 15 minutes. The slope was used to determine the rate of activity. Activity of each variant was normalized to the parent enzyme control from each plate.

Example 3: C16

Lipase activity was measured by following release of p-nitrophenol following hydrolysis of 4-nitrophenyl palmitate (pNP-C16). By linking a fatty acid to the p-nitrophenol it is possible to follow lipolytic activity by detecting the liberation of p-nitrophenol at 405 nm. Lipases were expressed and the secreted lipase separated from the cells by centrifugation. The supernatants were added to the assay buffer (pNP-C16, Hepes pH 7.5, Sorbitol, Triton X100, and BPER) in 96-well plate format. The absorbance at 405 nm was detected every 30 seconds for 2 to 15 minutes. The slope was used to determine the rate of activity. Activity of each variant was normalized to the parent enzyme control from each plate.

Example 4: Lipase Variant Expression

The variant lipase enzymes were obtained by constructing expression plasmids containing the encoding polynucleotide sequences, transforming plasmids into *Pichia pastoris*(*K-omagataella phaffii*) and growing the resulting expression strains in the following way. Fresh *Pichia pastoris* cells of the expression strains were obtained by spreading the glycerol stocks of sequence-confirmed strains onto yeast extract Peptone Dextrose (YPD) agar plates containing Zeocin. After 2 days, starter seed cultures of the production strains were inoculated into 100 mL of Buffered Glycerol Complex Medium (BMGY) using cells from these plates, and grown for 20-24 hours at 30° C. and 225-250 rpm. Seed cultures were scaled up by transferring suitable amounts into 2-4 L of BMMY medium in a baffled Fermenter. Fermentations were carried out at 30° C. and under 1100 rpm of agitation, supplied via flat-blade impellers, for 48-72 hours. After the initial batch-phase of fermentation, sterile-filtered Methanol was added as feed whenever the dissolved oxygen level in the culture dipped below 30%. Alternatively, feed was added every 3 hours at 0.5% v/v of the starting batch culture. The final fermentation broth was centrifuged at 7000×g for 30 mins at 4° C. to obtain the cell-free supernatant.

Expression levels of the variant lipase were determined as follows: supernatant was assayed for protein of interest expression by either SDS-PAGE or capillary electrophoresis and by enzymatic activity using PNP-octanoate as substrate.

Example 5: Lipase Variants Single Point Mutations

A parent lipase (SEQ ID NO: 1/2), was selected and used to generate non-naturally occurring variant lipase enzymes using Gene Site Saturation Mutagenesis (GSSM) as described in at least U.S. Pat. Nos. 6,171,820; 6,562,594; or 6,764,835. The lipase variants include all 19 amino acid substitutions at every amino acid reside over the full length of the amino acid sequence of SEQ ID NO:1/2. Supernatants of the variant lipase enzymes from the GSSM library were screened in 384 plate formats. The variant enzymes in supernatant was added to lard in 0.01% surfactant blend (2:5:3 of linear alkylbenzene sulfonate (Meranil DSB/E): sodium laureth sulfate 2EO (TexaponN70): alkyl polyethyleneglycol ether (LutensolA07)) in 100 mM Hepes pH8. Hits were defined as supernatants that hydrolyzed more lard than the parent measured by OD600. The lipase variants that have an improved characteristic when compared to the parent lipase were identified and the results are shown in Table 1, below. Lipase variants were identified that had improved characteristics such as higher activity, improved performance (stain removal on cloth), stability against proteolytic degradation, pH profile, higher expression, or any combination thereof when compared to the parent enzyme. The results listed below describe lipase variants having improved characteristics when compared to the parent lipase enzyme (SEQ ID NO:1/2). The lipase variants can also contain different amino acid substitutions at the same amino acid residue position number. For example, lipase variants at position 64 can be: K64V, K64T, or K64E, wherein either lipase variant has an improved characteristic when compared to the parent lipase.

TABLE 1

| Lipase No. | Original Amino Acid | Amino Acid Residue | New Amino Acid |
| --- | --- | --- | --- |
| LV005 | K | 14 | E |
| LV074 | F | 56 | C |
| LV008 | K | 64 | V |
| LV075 | K | 64 | T |
| LV076 | K | 64 | E |
| LV077 | P | 67 | L |
| LV078 | W | 79 | F |
| LV079 | W | 79 | i |
| LV080 | K | 145 | W |
| LV081 | K | 145 | E |
| LV082 | E | 263 | L |
| LV083 | I | 265 | T |
| LV084 | I | 265 | L |
| LV085 | Y | 266 | L |
| LV086 | Y | 266 | V |
| LV087 | N | 272 | P |
| LV088 | R | 273 | Q |
| LV089 | Y | 275 | F |
| LV090 | p | 287 | R |
| LV091 | N | 291 | A |
| LV092 | N | 291 | L |
| LV006 | N | 291 | F |
| LV007 | A | 293 | V |
| LV093 | F | 297 | L |
| LV009 | M | 298 | F |
| LV012 | A | 303 | Q |
| LV094 | S | 307 | L |
| LV095 | L | 308 | S |
| LV096 | L | 308 | N |
| LV097 | T | 310 | Q |
| LV098 | Y | 340 | F |
| LV099 | Y | 347 | K |
| LV100 | V | 375 | G |
| LV101 | Q | 377 | K |
| LV011 | L | 407 | A |
| LV010 | L | 407 | G |

Example 6: Lipase Variant Combinations of Mutations

Additional non-naturally occurring lipase variants were generated by combining the single point mutations from the previous example using a method of Tailored Multi-Site Combinatorial Assembly (TMSCA) as described in WO2009/018449. The lipase variants were identified that had improved characteristics such as higher activity, improved performance (stain removal on cloth), higher expression, stability against proteolytic degradation, or any combination thereof when compared to the parent enzyme. The combinations of amino acid mutations when compared to the parent enzyme are shown in the Table 2 below.

TABLE 2

| Polypeptide Variant Lipase Enzyme | Lipase Number |
| --- | --- |
| none - parent backbone | SEQ ID NO: 1 |
| N291A, 405L | LV001 |
| W79F, I265L, N291L | LV002 |
| E263L, T310Q | LV003 |
| T310Q, L407A | LV013 |
| K145E, L407A | LV014 |
| K64V, L407A | LV015 |
| M298F, L407A | LV016 |

TABLE 2-continued

| Polypeptide Variant Lipase Enzyme | Lipase Number |
|---|---|
| K145E, Y340F | LV017 |
| T310Q, L407A, K64V, K145E | LV018 |
| T310Q, L407A, K145E, M298F | LV019 |
| K14E, K64V, K145E, T310Q, L407A | LV020 |
| K64V, K145E, M298F, T310Q, L407A | LV021 |
| E263L, F297L, T310Q, L407A | LV022 |
| E263L, F297L, T310Q, L407G | LV023 |
| P67L, E263L, F297L, T310Q, | LV024 |
| F297L, T310Q | LV025 |
| E263L, F297L | LV026 |
| E263L, Q377K, T310Q, L407A | LV027 |
| E263L, Q377K, T310Q, L407G | LV028 |
| K14E, E2363L, I265T, A303Q, T310Q | LV029 |
| E263L, T310Q, L407A | LV030 |
| E263L, T310Q, L407G | LV031 |
| E263L, M298F, T310Q | LV032 |
| K145E, E263L, A303Q, T310Q, L407A | LV033 |
| K145E, E263L, A303Q, T310Q, L407G | LV034 |
| K64V, K145E, E263L, A303Q, T310Q | LV035 |
| K145E, E263L, A303Q | LV036 |
| K145E, A303Q | LV037 |
| K145E, Y340F, Y347K, L407A | LV038 |
| K145E, T310Q | LV039 |
| K145E, E263L | LV040 |
| K145E, Y347K | LV041 |
| K145E, K64V | LV042 |
| K145E, Y266L, A303Q | LV043 |
| K145E, E263L, M298F, T310Q, L407A | LV044 |
| K145E, E263L, M298F, T310Q, L407G | LV045 |
| K145E, E263L, T310Q, L407A | LV046 |
| K145E, E263L, T310Q, L407G | LV047 |
| K14E, A303Q, L407A | LV048 |
| K14E, E263L, A303Q, T310Q, L407A | LV049 |
| K145W, E263L, I265T, A303Q, T310Q, L407A | LV050 |
| K145W, I265T, A303Q, L407A | LV051 |
| K64V, K145W, E263L, T310Q, L407A | LV052 |
| K64V, K145W, E263L, M298F, T310Q | LV053 |
| K64V, K145W, E263L, Y266L, T310Q | LV054 |
| A303Q, L407A | LV055 |
| M298F, L407G | LV056 |
| I265T, M298F, L407A | LV057 |
| I265T, M298F, L407G | LV058 |
| Y266L, M298F, L407A | LV059 |
| Y266L, M298F, L407G | LV060 |
| P67L, F297L, L407A | LV061 |
| P67L, F297L, L407G | LV062 |
| I265T, L407A | LV063 |
| Y266L, L407G | LV064 |
| E263L, L407A | LV065 |
| K145E, Y340F | LV066 |
| K145E, Y340F, M298F, L407A | LV067 |
| K145E, Y340F, K64V, L407A | LV068 |
| K14E, A303Q, L407A, K145E | LV069 |
| K14E, A303Q, L407A, K145E, Y340F | LV070 |
| K14E, A303Q, L407A, M298F | LV071 |
| K14E, K64V, K145E, M298F, T310Q, L407A | LV072 |
| T312Q | LV073 |

The results for the improved characteristics of the polypeptide lipase variant enzymes are shown in the Table 3, below as a percentage when compared to the parent enzyme (SEQ ID NO:1/2).

TABLE 3

| Lipase | ELISA | pNPC8 | C16 |
|---|---|---|---|
| SEQ ID NO: 1 | 100% | 100% | 100% |
| LV013 | 140% | 37% | 103% |
| LV014 | 146% | 93% | 89% |
| LV015 | 84% | 53% | 69% |
| LV016 | 98% | 100% | 95% |
| LV017 | 122% | 91% | 91% |
| LV018 | 256% | 30% | 249% |
| LV019 | 168% | 32% | 164% |
| LV020 | 142% | 25% | 227% |
| LV021 | 361% | 28% | 168% |
| LV022 | 0% | 0% | 2% |
| LV023 | 0% | 0% | 1% |
| LV024 | 3% | 2% | 7% |
| LV025 | 46% | 25% | 71% |
| LV026 | 5% | 20% | 11% |
| LV027 | 13% | 1% | 8% |
| LV028 | 5% | 2% | 5% |
| LV029 | 22% | 47% | 40% |
| LV030 | 8% | 49% | 12% |
| LV031 | 6% | 3% | 17% |
| LV032 | 14% | 1% | 5% |
| LV033 | 9% | 10% | 18% |
| LV034 | 5% | 7% | 15% |
| LV035 | 15% | 45% | 27% |
| LV036 | 22% | 49% | 18% |
| LV037 | 147% | 100% | 89% |
| LV038 | 41% | 60% | 41% |
| LV039 | 89% | 14% | 45% |
| LV040 | 32% | 111% | 97% |
| LV041 | 14% | 35% | 20% |
| LV042 | 97% | 102% | 110% |
| LV043 | 142% | 106% | 124% |
| LV044 | 39% | 18% | 48% |
| LV045 | 34% | 12% | 40% |
| LV046 | 29% | 12% | 51% |
| LV047 | 15% | 10% | 47% |
| LV048 | 130% | 107% | 63% |
| LV049 | 10% | 9% | 14% |
| LV050 | 1% | 100% | 100% |
| LV051 | 47% | 74% | 67% |
| LV052 | 19% | 47% | 47% |
| LV053 | 27% | 95% | 114% |
| LV054 | 15% | 31% | 20% |
| LV055 | 110% | 83% | 76% |
| LV056 | 107% | 118% | 90% |
| LV057 | 51% | 53% | 48% |
| LV058 | 180% | 75% | 71% |
| LV060 | 150% | 31% | 25% |
| LV061 | 0% | 1% | 3% |
| LV062 | 0% | 1% | 2% |
| LV063 | 31% | 44% | 49% |

TABLE 3-continued

| Lipase | ELISA | pNPC8 | C16 |
|---|---|---|---|
| LV064 | 54% | 53% | 75% |
| LV065 | 16% | 30% | 19% |
| LV066 | 112% | 82% | 65% |
| LV068 | 153% | 81% | 103% |
| LV069 | 126% | 74% | 68% |
| LV070 | 141% | 77% | 65% |
| LV071 | 92% | 72% | 38% |
| LV072 | 188% | 27% | 158% |

Example 7: Fat-Removal Performance

The lipase variant polypeptides were tested in a at small scale on the following stains: 1)C-S-61: beef fat on cotton, Lab values before wash; 2) EMPA112: lard on cotton, Lab values before wash. Producer: Center for Testmaterials (CFT) BV, NL-3130 AC Vlaardingen.

Stained swatches were put into open cylindric [stainless steel] vessels (ratio height to diameter 1:1 to 3:1) of a size <2000 microL, filling rate <80%, and containing one of the following types of washing liquor: (a) Detergent in water (hardness 2.5 mmol/L; $Ca^{2+}$: $Mg^{2+}$: $HCO_3^+$=4:1:8); (b) Detergent in water+lipase (different concentrations in ppm).

The stained swatches were shaken in the washing liquor at a fabric/liquor ration of 1:35 on shaking table devices at the selected temperature for 20 min. After the wash, the swatches were rinsed under continuous tap water (12-21° dH) flow (2-6 l/min) for <5 min. The rinsed swatches were dried under continuous air stream and stored in a dark closed room under ambient condition until they are measured.

The stain removal performance was determined by using the MACH5 multi area color measurement which gives LAB values and ΔE calculated between unwashed and washed stain.

The brightness L *, the value a * on the red-green color axis and the b * value on the yellow-blue color axis, were measured by using MACH 5 multi area color measurement (Center for Testmaterials (CFT) BV, NL-3130 AC Vlaardingen) before and after washing. The change of the color value (ΔE) value. ΔE was measured according to CIELAB color space, defined and calculated automatically by the evaluation color tools on the following equation: ΔE=root (Δ Delta a * 2+Δ Delta b * 2+Δ Delta L * 2). ΔE is a measure of the achieved stain removal effect or washing effect. All measurements were repeated 2 times to yield an average number. Note that higher ΔE values represent better washing effects when compared to lower ΔE values.

The results are also outlined below in Table 4, trials 1 to 4.

Example 8: Fat Stain Removal with Launder-o-Meter (LOM)

The lipase variant polypeptides were tested in with a LOM. Selected stain monitors were washed together with cotton ballast fabric and steel balls at 25° C. in wash liquor using base formulation ES1 or ES4 in the launder-o-meter (LP2 Typ, SDL Atlas Inc., USA) under the following washing conditions:

ES1 Detergent Formulation:

| component | type | A Conc [%] |
|---|---|---|
| Lutensit A-LBS | LAS | 5.5 |
| Edenor coco fatty acid | $C_{12}$-$C_{18}$ coco fatty acid | 2.4 |
| Lutensol AO7 | AEO | 5.5 |
| Texapon N70 | FAEO | 5.5 |
|  | 1,2 propylene glycol | 6.0 |
|  | ethanol | 2.0 |
|  | KOH | 2.2 |

ES4 Detergent Formulation:

| component | type | A Conc [%] |
|---|---|---|
| Lutensit A-LBS | LAS | 3.63 |
| Edenor coco fatty acid | $C_{12}$-$C_{18}$ coco fatty acid | 2.67 |
| Lutensol AO 7 | AEO | 7.62 |
| Texapon N70 | FAEO | 10.37 |
|  | 1,2 propylene glycol | 4.45 |
|  | ethanol | 1.48 |
|  | KOH | 2.45 |

Test Conditions

| | |
|---|---|
| Washing liquor | 250 ml |
| # Steel balls* | 20 |
| Washing time/temperature | 20 min at 25° C. or 40° C. |
| Dosage Lipase | Either 0 ppm, 0.2 ppm or 1.5 ppm |
| Dosage detergent | 2 g/L or 5 g/L |
| Washing cycles | 1 |
| Water hardness | 2.5 mmol/L; |
| Ballast fabric | 15 g cotton fabric 283 |
| Sum ballast + soiled fabric | 20 g |
| Soiled swatches | 2 × 2.5 g C-S-61 or C-S 62 |
| Fabric/liquor ratio | 1:12.5 |

After the washing, the fabrics were rinsed, spin-dried and dried in the air. The washing performance for the single stains is determined by measuring the remission value of the soiled fabric after wash with the spectrophotometer from Fa. Datacolor (Elrepho 2000) at 460 nm. In general, the higher the remission value, the better the performance. For the multi soil monitors the stain removal performance was determined by using the MACH5 multi area color measurement which gives LAB values and ΔE calculated between unwashed and washed stain (calculation according to example 7). The results are also outlined below in Table 4, trials 5 to 8.

Single Trials:

Trial 1: Cotton soiled with Beef fat (CFT-CS 61), 2 g/L ES 4 (30%), 25° C., small scale, ΔE at 1.5 ppm.

Trial 2: Cotton soiled with Beef fat (CFT-CS 61), 2 g/L ES 4 (30%), 40° C., small scale, ΔE at 1.5 ppm.

Trial 3: Beef fat (CFT-CS 61), 2 g/L ES 1 (20%), 25° C., small scale, ΔE at 1.5 ppm.

Trial 4: Beef fat (CFT-CS 61), 2 g/L ES 1 (20%), 40° C., small scale, ΔE at 1.5 ppm.

Trial 5: Cocoa (EMPA 112), 2 g/L ES 4 (30%), 25° C., LOM, ΔE at 1.5 ppm.

Trial 6: Polyester/Cotton soiled w/Pigment/Sebum (wfk 20D), 2 g/L ES 4 (30%), 25° C., LOM, ΔE at 1.5 ppm.

Trial 7: Polyester/Cotton soiled w/Pigment/Sebum (wfk 20D), 2 g/L ES 1 (20%), 25° C., LOM, ΔE at 1.5 ppm.

Trial 8: Cotton soiled with chocolate mousse (CFT CS-70), 2 g/L ES 1 (20%), 25° C., LOM, ΔE at 1.5 ppm.

TABLE 4

Wash performance (in ΔEE) of lipase variants on fat stains (normalized) ND = no data generated

| Lipase | Trial 1 | Trial 2 | Trial 3 | Trial 4 | Trial 5 | Trial 6 | Trial 7 | Trial 8 |
|---|---|---|---|---|---|---|---|---|
| SEQ ID NO: 1/2 | 100 | 100 | 100 | 100 | 100 | 100 | 100 | 100 |
| LV004 | 71 | 106 | ND | ND | ND | ND | ND | ND |
| LV005 | 120 | 99 | ND | ND | ND | ND | ND | ND |
| LV006 | 104 | 101 | ND | ND | ND | ND | ND | ND |
| LV007 | 96 | 100 | 38 | 49 | ND | 120 | ND | ND |
| LV008 | 228 | 205 | 110 | 113 | ND | 194 | ND | ND |
| LV009 | 248 | 211 | 109 | 116 | ND | 180 | ND | ND |
| LV010 | 195 | 206 | 107 | 110 | ND | 178 | ND | ND |
| LV011 | 195 | 205 | 95 | 100 | 102 | 197 | 97 | 110 |
| LV012 | 101 | 147 | ND | ND | 92 | 188 | 107 | 100 |
| LV013 | 77 | 99 | ND | ND | 92 | 175 | 88 | 100 |
| LV014 | 110 | 112 | ND | ND | 93 | 186 | 88 | 101 |
| LV015 | 95 | 106 | ND | ND | 86 | 184 | 87 | 100 |
| LV016 | 109 | 106 | ND | ND | 90 | 193 | 96 | 93 |
| LV017 | 116 | 133 | 123 | 105 | ND | ND | ND | ND |
| LV018 | 111 | 116 | 111 | 91 | ND | ND | ND | ND |
| LV019 | 102 | 115 | 117 | 97 | ND | ND | ND | ND |
| LV020 | 94 | 101 | 107 | 94 | ND | ND | ND | ND |
| LV021 | 83 | 109 | 107 | 92 | ND | ND | ND | ND |
| Detergent alone | 100 | 100 | 89 | 97 | 43 | 100 | 72 | 92 |

Trials 1 and 2: Lipase variants LV005, LV006, LV008, LV009, LV010, LV011, LV014, LV016, LV017, LV018, LV019 with significant performance increase on stain beef fat compared to parent lipase enzyme (SEQ ID NO:1/2). Variants LV008, LV009, LV010, LV011 with twice the performance of parent lipase enzyme on stain beef fat at 25° C. and 40° C. in detergent ES4 (2 g/l), when dosed at 1.5 ppm of the enzymes in high-throughput wash.

Trials 3 and 4: Performance benefits confirmed in detergent ES1 under same conditions at 25° C. and 40° C. with 2 g/l wash detergent and 1.5 ppm enzyme dosage against SEQ ID NO:1.

Trial 6: Variants LV008, LV009, LV010, LV011, LV012, LV013, LV014, LV015, and LV016 with performance benefits when compared to the parent lipase enzyme of SEQ ID NO:1/2, on stain pigment/sebum on polyester/cotton at 25° C. wash temperature in detergent ES 4 (2 g/l) in LOM.

Example 9: Fatty Acid Selectivity

Lipase activity was measured by following release of p-nitrophenol following hydrolysis of 4-nitrophenyl butyrate (pNP-C4), 4-nitrophenyl caprylate (pNP-C8), 4-nitrophenyl laurate (pNP-C12), 4-nitrophenyl myristate (pNP-C14), 4-nitrophenyl palmitate (pNP-C16), and 4-nitrophenyl stearate (pNP-C18). By linking a fatty acid to the p-nitrophenol it is possible to follow lipolytic activity by detecting the liberation of p-nitrophenol at 405 nm. Lipases were expressed and the secreted lipase separated from the cells by centrifugation. The supernatants were added to the assay buffer (pNP substrate, Hepes pH 7.5, Sorbitol, Triton X100, and BPER) in 96-well plate format. The absorbance at 405 nm was detected every 30 seconds for 2 to 15 minutes. The slope was used to determine the rate of activity. Selectivity is reported as activity across the different pNP substrates and the results are shown in FIG. 1.

Example 10: Lipase Variants Stability in the Presence of Protease

The lipase variants were tested for stability in the presence of protease.

Figure 2:
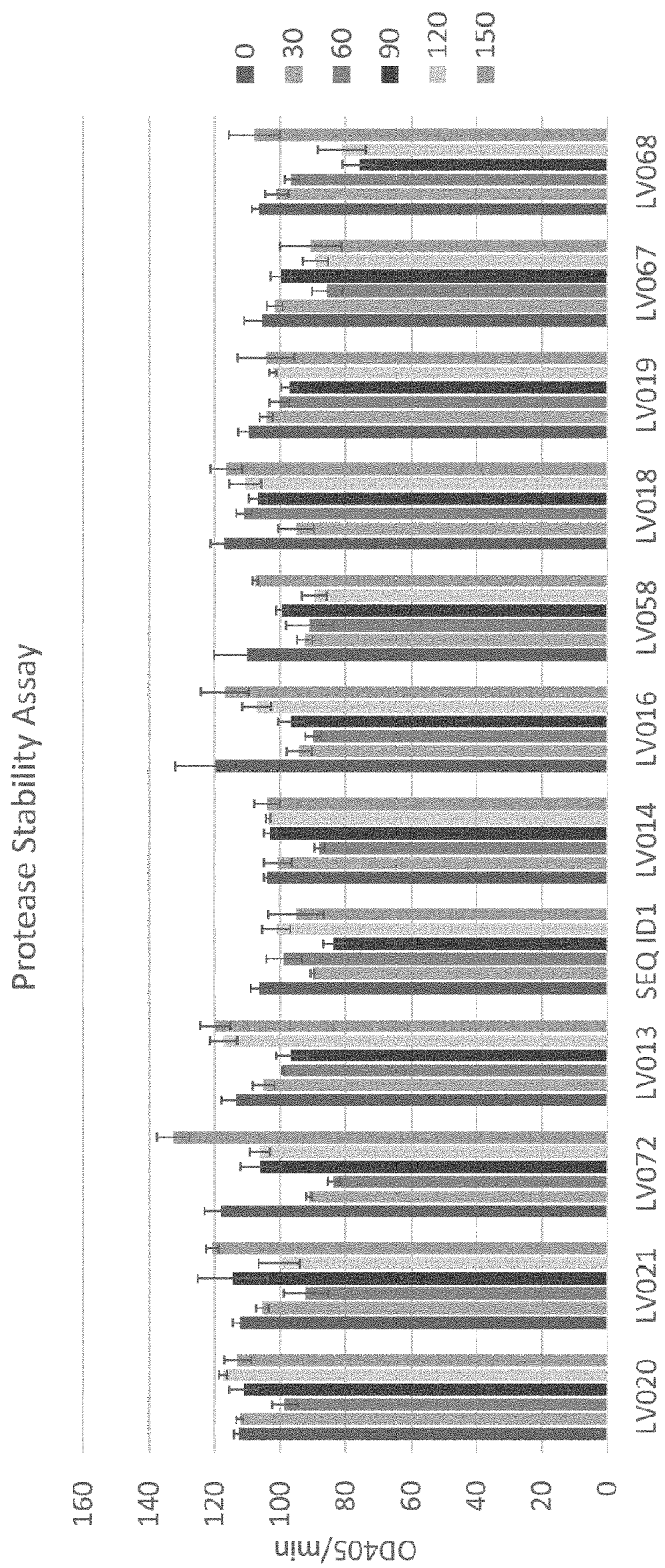
FIG. 2, show activity of lipase enzymes stability in the presence of protease.

Stability of Lipase in presence of protease (Detralase) in Tris Buffer pH 8.6, samples stored at 37° C., Lipase assay, Detralase 1% w/w. The results shown in FIG. 2, show that the lipase variants retain activity after 80 minutes when compared to the lipase according to SEQ ID NO: 1. The lipase variants have different activity when compared to the parent lipase enzyme (SEQ ID NO.: 1/2) in the presence of protease.

Further, the stability of Lipase of SEQ ID NO: 1 in presence of various proteases has been tested in detergent formulation. Table Comp.:

| Component | % w/w |
|---|---|
| Lutensit A-LBS | 5.7 |
| 1,2 Propylenglykol | 6 |
| Edenor palmitic/oleic acid K12-18 | 2.4 |
| KOH | 3.1 |
| Texapon N70 | 7.7 |
| Lutensol AO 7 | 5.4 |
| Ethanol | 2 |
| Water | 57.7 |
| total: | 90 |
| Aesthetics, physical stability | Clear, stable |

The protease activity was determined using Succinyl-Ala-Ala-Pro-Phe-p-Nitroanilide (Suc-AAPF-pNA, short: AAPF; see e.g. DelMar et al. (1979), Analytical Biochem 99, 316-320) as substrate. pNA is cleaved from the substrate molecule. The rate of cleavage can be determined by the increase of the yellow color of free pNA in the solution by measuring OD405, the optical density at 405 nm.

BLAP wildtype (SEQ ID NO:22 as described in EP 1921147) and BLAP variant (SEQ ID NO:22 as described in EP 1921147 having amino acid substitution R99E) were added to detergent formulation at a dosage of 1% w/w (see Table Comp. above) and thoroughly mixed. In addition, 0.3% of the lipase was added. Samples were taken at indicated time points and kept frozen until all samples were taken. All samples were measured at the end of the study with AAPF Assay.

Lipase activity was tested using a lipase assay based on the synthetic substrate p-Nitrophenolvalerate.

Enzymatic Activities in a Composition Comprising Lipolase and Protease:

| | Days | | | | | |
|---|---|---|---|---|---|---|
| | 0 | 2 | 7 | 14 | 21 | 28 |
| | Lipolase activity after X days storage [%] | | | | | |
| BLAP WT, R99 | 100 | 13 | 1 | 0 | 0 | 0 |
| BLAP variant, R99E | 100 | 63 | 45 | 33 | 21 | 18 |

Enzymatic Activities in a Composition Comprising Letra Lip and Protease:

|  | Days | | | | | |
|---|---|---|---|---|---|---|
|  | 0 | 2 | 7 | 14 | 21 | 28 |
|  | Letra Lip activity after X days storage [%] | | | | | |
| BLAP WT, R99 | 100 | 11 | 1 | 1 | 0 | 0 |
| BLAP variant, R99E | 100 | 81 | 47 | 27 | 16 | 12 |

Enzymatic Activities in a Composition Comprising Lipase (SEQ ID NO: 1) and Protease:

|  | Days | | | | | |
|---|---|---|---|---|---|---|
|  | 0 | 2 | 7 | 14 | 21 | 28 |
|  | Lipase (SEQ ID NO: 1) activity after X days storage [%] | | | | | |
| BLAP WT, R99 | 100 | 38 | 0 | 0 | 0 | 0 |
| BLAP variant, R99E | 100 | 91 | 76 | 49 | 42 | 31 |

The data shop that the lipase according to SEQ ID NO: 3 are more stable in a detergent formulation comprising BLAP variant, R99E protease when compared to Lipolase and Letra Lip.

The invention claimed is:

1. A polypeptide having lipase activity comprising an amino acid sequence that has at least 90% sequence identity to the full length amino acid sequence of SEQ ID NO:1, wherein the polypeptide comprises at least one amino acid residue substitution at an amino acid residue position number 14, 64, 67, 145, 263, 265, 266, 291, 293, 297, 298, 303, 310, 347, 377 or 407, based on the amino acid sequence of SEQ ID NO:1.

2. The polypeptide of claim 1, wherein the at least one amino acid residue substitution is one of the following: K14E, K64V, K64T, K64E, P67L, K145W, K145E, E263L, I265T, I265L, Y266L, Y266V, N291A, N291L, N291F, A293V, F297L, M298F, A303Q, T310O, Y347K, Q377K, L407A, or L407G, based on the amino acid sequence of SEQ ID NO:1.

3. The polypeptide of claim 2, wherein the polypeptide has a combination of amino acid modifications to the amino acid sequence of SEQ ID NO:1, and the combination is selected from the group consisting of: (a1) N291A, 405L; (b1) W79F, I265L, N291L; (c1) E263L, T310Q; (d1) T310Q, L407A; (e1) K145E, L407A; (f1) K64V, L407A; (g1) M298F, L407A; (h1) K145E, Y340F; (i1) T310Q, L407A; (j1) T310Q, L407A; (k1) K14E, K64V, K145E, T310Q, L407A; (n1) K64V, K145E, M298F, T310Q, L407A; (m1) E263L, F297L, T310Q, L407A; (n1) E263L, F297L, T310Q, L407G; (o1) P67L, E263L, F297L, T310Q; (p1) F297L, T310Q; (q1) E263L, F297L; (r1) E263L, Q377K, T310Q, L407A; (s1) E263L, Q377K, T310Q, L407G; (t1) K14E, E2363L, I265T, A303Q, T310Q; (u1) E263L, T310Q, L407A; (v1) E263L, T310Q, L407G; (w1) E263L, M298F, T310Q; (x1) K145E, E263L, A303Q, T310Q, L407A; (y1) K145E, E263L, A303Q, T310Q, L407G; (z1) K64V, K145E, E263L, A303Q, T310Q; (a2) K145E, E263L, A303Q; (b2) K145E, A303Q; (c2) K145E, Y340F, Y347K, L407A; (d2) K145E, T310Q; (e2) K145E, E263L; (f2) K145E, Y347K; (g2) K145E, K64V; (h2) K145E, Y266L, A303Q; (i2) K145E, E263L, M298F, T310Q, L407A; (j2) K145E, E263L, M298F, T310Q, L407G; (k2) K145E, E263L, T310Q, L407A; (l2) K145E, E263L, T310Q, L407G; (m2) K14E, A303Q, L407A; (n2) K14E, E263L, A303Q, T310Q, L407A; (O2) K145W, E263L, I265T, A303Q, T310Q, L407A; (p2) K145W, I265T, A303Q, L407A; (q2) K64V, K145W, E263L, T310Q, L407A; (r2) K64V, K145W, E263L, M298F, T310Q; (s2) K64V, K145W, E263L, Y266L, T310Q; (t2) A303Q, L407A; (u2) M298F, L407G; (v2) I2651, M298F, L407A; (w2) I2651, M298F, L407G; (x2) Y266L, M298F, L407A; (y2) Y266L, M298F, L407G; (z2) P67L, F297L, L407A; (a3) P67L, F297L, L407G; (b3) I2651, L407A; (c3) Y266L, L407G; (d3) E263L, L407A; (e3) K145E, Y340F; (f3) K145E, Y340F; (g3) K145E, Y340F; (h3) K14E, A303Q, L407A; (i3) K14E, A303Q, L407A; (j3) K14E, A303Q, L407A; and (k3) K14E, K64V, K145E, M298F, T310O, L407A.

4. The polypeptide of claim 1, wherein the polypeptide has an increase in enzyme activity, pH-stability, stability against proteolytic degradation, or any combination thereof when compared to the lipase of SEQ ID NO:1.

5. The polypeptide as in claim 1, wherein the polypeptide is a fragment of the full length amino acid sequence and the fragment has lipase activity.

6. A composition comprising the polypeptide as in claim 1.

7. The composition of claim 6, comprising a second enzyme selected from the group consisting of: a second lipase, an amylase, a protease, a cellulase, a laccase, a pectinase, and a nuclease.

8. The polypeptide of claim 1, comprising an amino acid sequence that has at least 93% sequence identity to the full length amino acid sequence of SEQ ID NO:1.

9. The polypeptide of claim 1, comprising an amino acid sequence that has at least 95% sequence identity to the full length amino acid sequence of SEQ ID NO:1.

10. The polypeptide of claim 1, comprising an amino acid sequence that has at least 98% sequence identity to the full length amino acid sequence of SEQ ID NO:1.

11. The polypeptide of claim 1, comprising an amino acid sequence that has at least 99% sequence identity to the full length amino acid sequence of SEQ ID NO:1.

* * * * *